(12) United States Patent  (10) Patent No.: US 6,746,426 B1
Flaherty et al.  (45) Date of Patent: Jun. 8, 2004

(54) TRANSLUMINALLY DELIVERABLE VASCULAR BLOCKERS AND METHODS FOR FACILITATING RETROGRADE FLOW OF ARTERIAL BLOOD THROUGH VEINS

(75) Inventors: J. Christopher Flaherty, Topsfield, MA (US); Theodore C. Lamson, Pleasanton, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 09/613,675

(22) Filed: Jul. 11, 2000

(51) Int. Cl.[7] ............................................. A61M 29/00
(52) U.S. Cl. ................................... 604/104; 604/96.01
(58) Field of Search .......................... 604/104, 96.01, 604/164.13, 264, 523, 528, 532

(56) References Cited

U.S. PATENT DOCUMENTS

| | | | | |
|---|---|---|---|---|
| 5,370,685 A | * | 12/1994 | Stevens ....................... | 623/2.11 |
| 5,449,372 A | * | 9/1995 | Schmaltz et al. ........... | 606/198 |
| 5,584,803 A | * | 12/1996 | Stevens et al. .............. | 604/4 |
| 5,885,238 A | * | 3/1999 | Stevens et al. ............. | 604/6.14 |
| 5,957,949 A | | 9/1999 | Leonhardt et al. ........... | 606/194 |
| 6,035,856 A | | 3/2000 | LaFontaine et al. ........ | 128/898 |
| 6,070,589 A | * | 6/2000 | Keith et al. .................. | 128/898 |
| 6,248,086 B1 | * | 6/2001 | Sweezer et al. ........... | 604/4.01 |
| 6,299,637 B1 | * | 10/2001 | Shaolian et al. ........... | 623/1.24 |
| 6,340,356 B1 | * | 1/2002 | Navia et al. ................. | 604/104 |
| 6,350,252 B2 | * | 2/2002 | Ray et al. .................... | 604/107 |
| 6,352,561 B1 | * | 3/2002 | Leopold et al. ............. | 623/123 |
| 6,425,898 B1 | * | 7/2002 | Wilson et al. .............. | 606/108 |
| 6,440,164 B1 | * | 8/2002 | DiMatteo et al. .......... | 623/1.24 |
| 6,443,922 B1 | * | 9/2002 | Roberts et al. ............. | 604/4.01 |

* cited by examiner

Primary Examiner—Thomas Denion
Assistant Examiner—Ching Chang
(74) Attorney, Agent, or Firm—Robert D. Buyan; Stout, Uxa, Buyan & Mullins, LLP

(57) ABSTRACT

Transluminal methods and apparatus for causing arterial blood to flow through a vein of a mammalian patient, in a direction opposite normal venous blood flow, after an arterial blood containing conduit has been purposely or inadvertently connected to the vein. The method includes the use of a transluminally inserted vessel lumen occluding apparatus to at least partially block (e.g., occlude, embolize or close) the lumen of the vein at a location that is proximal to the location at which the arterial blood containing conduit is connected to the vein. The apparatus comprises a radially expandable lumen blocking device that is implantable in the vein lumen and catheters and other apparatus for implanting the radially expandable lumen blocking device into the lumen of the vein.

37 Claims, 22 Drawing Sheets

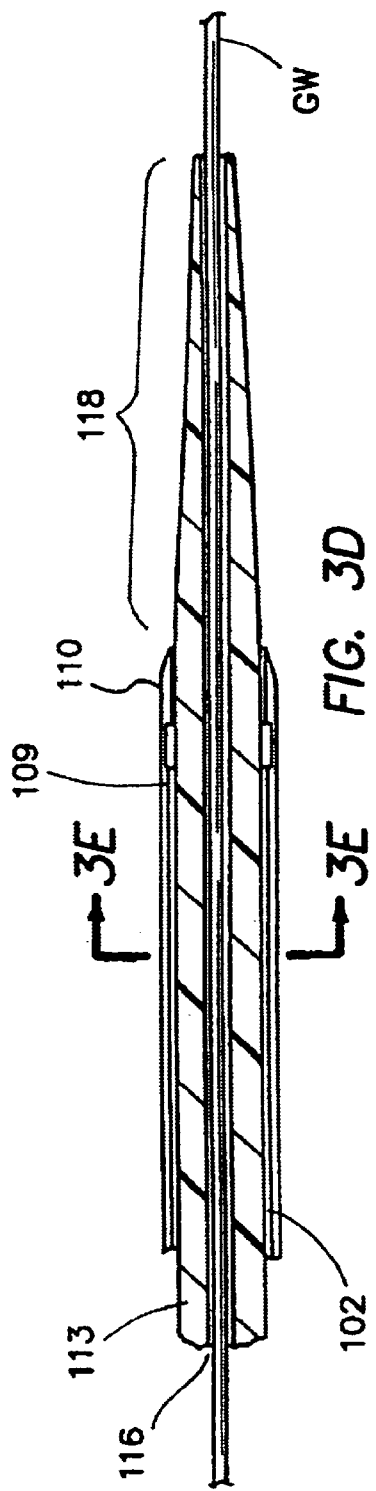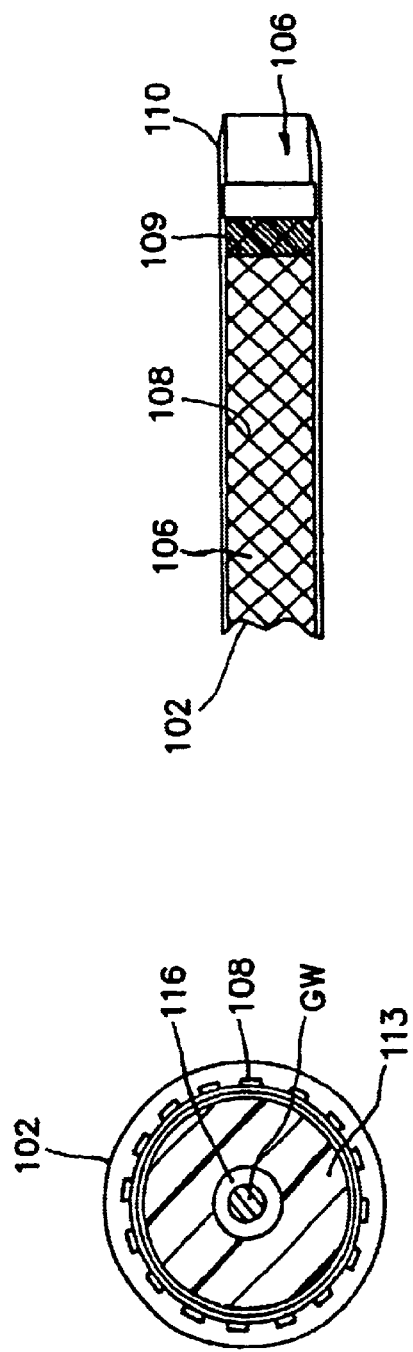
FIG. 3D
FIG. 3E
FIG. 3F

TRANSLUMINALLY DELIVERABLE VASCULAR BLOCKERS AND METHODS FOR FACILITATING RETROGRADE FLOW OF ARTERIAL BLOOD THROUGH VEINS

FIELD OF THE INVENTION

The present invention relates generally to medical devices and methods, and more particularly to transluminally implantable vascular blocking devices and methods for causing retrograde flow of arterial blood through veins to treat ischemia caused by insufficient arterial blood flow.

BACKGROUND OF THE INVENTION

Atherosclerotic cardiovascular disease remains a major cause of premature death and morbidity, in most regions of the world. In addition to drug therapy, there currently exist a number of surgical and interventional techniques for treating atherosclerotic cardiovascular disease. Among these are a number of revascularization procedures wherein arterial or oxygenated blood (i.e., blood that generally has a $pO_2$ of at least 50 and typically 75–100 while the patient is breathing room air) is rerouted or caused to flow in a manner that provides improved perfusion of ischemic tissues.

1. Surgical Bypass of Diseased Coronary or Peripheral Arteries

An arterial bypass graft operation is a type of surgery that is done to reroute or "bypass" blood around clogged arteries, thereby improving the supply of blood and oxygen to tissues that have become ischemic due to blockage(s) in the affected artery. During bypass surgery, surgeons take a blood vessel from another part of the body, or a synthetic or natural vascular graft, and construct a detour around the blocked part of a coronary or peripheral artery. In coronary artery bypass graft surgery (CABG) procedures performed to remedy an obstructed coronary artery, an artery (e.g., the right internal mammary artery or left internal mammary artery) may be detached from the chest wall and the open end of that detached artery is then attached to the coronary artery below the blocked area. Alternatively, a segment of a long vein may be harvested from the patient's leg (e.g, Saphenous Vein) or other area of the body and one end of that vein segment connected to the aorta and its other end is attached or "grafted" to the coronary artery below the blocked area.

Occasionally, because many coronary or cardiac veins are substantially parallel to coronary arteries, it happens that arterial bypass grafts are accidentally attached to a coronary or cardiac vein instead of the desired coronary artery. This results in the formation of inadvertent arterio-venous fistulas and resultant steal of arterial blood from the affected coronary vein due to shunt effect (i.e., oxygenated blood that has entered the vein flowing in the direction of normal venous bloodflow back to the right atrium instead of flowing in a direction opposite normal venous blood flow and perfusing the ischemic myocardium). These inadvertent arterio-venous fistulas have required corrective surgery to ligate the erroneously placed graft (thereby eliminating the shunt) and to create a new bypass graft that is connected to the intended coronary artery. see, Lawrie, G. M. et al., *Aortocoronary Saphenous Vein Autograft Accidentally Attached to a Coronary Vein: Follow-up Angiography and Surgical Correction of the Resultant Arteriovenous Fistula*, Ann. Thorac. Surg. 22:1 87–90 (1976).

Cardiovascular surgeons have also experimented with the purposeful use of cardiac veins for coronary revascularization. These coronary vein bypass graft (CVBG) procedures were typically performed on patients who had severely diffuse stenotic coronary artery disease that rendered them not to be candidates for mainstream CABG surgery. This CVBG technique involved using an intervening graft from the internal mammary artery or an aortic attachment to a saphenous vein graft. Instead of anastomosing the grafts to the distal coronary artery, the grafts were attached to coronary or cardiac veins that are generally parallel to the obstructed arteries. The coronary vein to which the graft is attached is then ligated proximal to the graft attachment to prevent a shunt. Thus, the veins were 'arterialized', allowing arterial blood to flow through the vein in a retrograde fashion in a effort to bring oxygenated blood to the venules and capillaries of the heart. However, the ligating of the vein proximal to the graft attachment (i.e., between the location at which the graft is anastomosed to the vein and the coronary venous sinus) often required dissection of the vein or tunneling under the vein to free the region of vein that is to be ligated from the myocardium. Such dissection and freeing of the vein can cause undesirable trauma to the myocardium. see, Hochberg, M. S., et al., *Selective Arterialization of Coronary Veins: Clinical Experience of 55 American Heart Surgeons*; Clinics of CSI; 1986, 1:195–201 (1986).

Furthermore, accomplishing a specific degree of partial or total closure of the vein can be difficult to accomplish by merely tying a ligature or suture around the vein. Indeed, if the ligature is drawn and tied too tightly the vein may be severed or perforated causing hemorrhage. On the other hand, if the ligature is drawn and tied too loosely the vein lumen may not become or remain permanently closed and the ligature may fail to stop the undesirable steal of arterial blood from the vein.

2. Catheter-Based Transluminal Procedures for Bypass of Diseased Coronary or Peripheral Arteries:

Included among the newer interventional techniques are certain percutaneous, transluminal techniques for bypassing obstructions in coronary or peripheral arteries through the use of the adjacent vein(s) as in situ bypass conduit(s); (e.g. using catheters to perform extraluminal procedures outside the diseased vessel lumen). These are proprietary procedures being developed by Transvascular, Inc. of Menlo Park, Calif. and are described in various publications including U.S. Pat. No. 5,830,222 (Makower) and U.S. Pat. No. 6,068,638 (Makower), as well as in published PCT Applications WO 98/16161 and WO 98/46119.

In one such procedure known as a Percutaneous In Situ Coronary Venous Arterialization (PICVA™), catheters are used to form an interstitial channel between a coronary artery or chamber of the heart and a coronary vein such that arterial or oxygenated blood (i.e., blood that generally has a $pO_2$ of at least 50 and typically 75–100 while the patient is breathing room air) will flow from the artery or chamber of the heart and into the vein. A blocker delivery catheter is advanced into the vein, proximal to the location at which the channel is formed (i.e., between the location at which the channel is formed and the coronary venous sinus), and a radially expandable vessel blocking device is deployed from the catheter such that it becomes implanted in the lumen of the vein. This vessel blocking device serves to substantially block the flow of blood through the vein in the proximal direction (i.e., the direction in which venous blood normally flows through the vein, thereby eliminating the shunt effect and causing the arterial blood to flow through the vein in the distal direction (i.e., the direction opposite normal venous blood flow).

In another procedure known as Percutaneous In Situ Coronary Artery Bypass (PICAB™), catheters are used to form a first interstitial channel between a coronary artery or chamber of the heart and a coronary vein such that arterial or oxygenated blood (i.e., blood that generally has a $pO_2$ of at least 50 and typically 75–100 while the patient is breathing room air) will flow from the artery or chamber of the heart and into the vein and a second interstitial channel between the vein into which the oxygenated blood is flowing and a distal segment of the obstructed coronary artery, downstream of the obstruction. A blocker delivery catheter is advanced into the vein and used to implant two (2) radially expandable vessel blockers, one proximal to the first interstitial channel (i.e., between the first channel and the coronary venous sinus) and another distal to the second interstitial channel (i.e., between the second channel and the capillary bed that is drained by the vein). The first vessel blocking device serves to substantially block the flow of blood through the vein in the proximal direction (the direction of normal venous blood flow), thereby eliminating the shunt effect and causing the arterial blood to flow through the vein in the distal direction (i.e., the direction opposite normal venous blood flow). The second vessel blocking device serves to cause the oxygenated blood that has been rerouted into the segment of vein between the first and second channels to flow through the second channel and into the obstructed artery, downstream of the obstruction. In this manner, oxygenated blood is caused to flow through the distal segment of the obstructed artery, thereby perfusing the previously ischemic tissue.

Although the prior art had included a number of embolic coils and other embolic devices for occluding blood vessels, those prior art embolic devices were not designed for use in arterialized veins and were found to be less than optimal for use in blocking arterialized veins in the PICVA and PICAB procedures. Accordingly, a number of specialized, transluminally insertable apparatus for closing the lumen of a blood vessel have been invented for use in the PICVA and PICAB procedures and are described in U.S. Pat. No. 6,071,292 (Makower et al.) entitled Transluminal Methods and Devices for Closing, Forming Attachments to, and/or Forming Anastomotic Junctions in Luminal Anatomical Structures and PCT International Publication Nos. WO97/27893 (Evard, et al.) entitled Methods and Apparatus for Blocking Flow Through Blood Vessels and WO99/49793 (Flaherty et al.) entitled Catheters, Systems and Methods for Percutaneous In Situ Arterio-Venous Bypass, the entire disclosures of which are expressly incorporated herein by reference. Given the potential usefulness of surgical CVBG procedures and the incidence of inadvertent arterio-venous fistula creation during CABG procedures, there exists a need in the art for the adaptation and use of the transluminally insertable lumen blocking apparatus such as those described in the aforementioned U.S. Pat. No. 6,071,292 (Makower et al.) and PCT International Publication Nos. WO97/27893 (Evard, et al.) and WO99/49793 (Flaherty et al.) in conjunction with surgical CVBG procedures and as a non-surgical means for eliminating "steal" of arterial blood from the vein and improving myocardial perfusion in patients who have experienced inadvertent arterio-venous fistula creation during CABG procedures.

SUMMARY OF THE INVENTION

The present invention provides percutaneous, transluminal (e.g., catheter-based) methods and devices for blocking the lumen of a vein into which oxygenated blood having a $pO_2$ of at least 50 has been or will be caused to flow, as a result of the inadvertent or purposeful creation of an arteriovenous fistula.

In accordance with the invention, there is provided a method for causing arterial blood to flow through a vein of a mammalian patient, in a direction opposite normal venous blood flow, said method comprising the steps of (a) purposefully or inadvertently connecting an arterial blood containing conduit (e.g., an artery, a tubular graft into which arterial blood will flow, a transmyocaridal or interstitial channel that is in fluid communication with a chamber of the left heart or other arterial blood source, etc.) to the vein such that arterial blood will flow from the arterial blood containing conduit into the vein, (b) transluminally inserting a lumen occluding device into the vein, and (c) using the transluminally inserted lumen occluding device to block the lumen of the vein at a location proximal to the location at which the arterial blood containing conduit is connected to the vein (i.e., in a coronary application, between the location at which the arterial blood containing conduit is attached to a coronary vein and the coronary venous sinus into which venous blood drains from the coronary vein). The lumen occluding apparatus used in steps b and c may be any suitable type of transluminally insertable apparatus that will cause a desired degree of blockage or closure of the vein lumen. One type of lumen occluding device that may be used in this method comprises a delivery catheter that deploys a radially expandable blocker device into the lumen of the vein, examples of which are specifically described in this patent application. Examples of other types of transluminally insertable lumen occluding apparatus useable in this method include, but are not limited to those described in U.S. Pat. No. 6,071,292 Makower et al.) entitled Transluminal Methods and Devices for Closing, Forming Attachments to, and/or Forming Anastomotic Junctions in Luminal Anatomical Structures and PCT International Publication Nos. WO97/27893 (Evard, et al.) entitled Methods and Apparatus for Blocking Flow Through Blood Vessels and WO99/49793 (Flaherty et al.) entitled Catheters, Systems and Methods for Percutaneous In Situ Arterio-Venous Bypass, the entire disclosures of which are expressly incorporated herein by reference.

Further in accordance with this invention, there are provided catheter-based devices and systems for implanting radially expandable lumen blocking devices into veins in accordance with the above-summarized method of the present invention. These systems generally comprise (a) a blocker delivery catheter that is transluminally advanced into the vein proximal to the location at which the arterial blood containing conduit is connected to the vein and (b) a radially expandable blocker that is deployable from the catheter such that the blocker radially expands and becomes implanted within the vein at a location proximal to the location at which the arterial blood containing conduit is connected to the vein (i.e., between the location at which the arterial blood containing conduit is attached to the vein and the coronary venous sinus into which venous blood drains from the coronary veins). The blocker delivery catheter may be a relatively long catheter (e.g., 40–125 cm in length) that is inserted into the venous vasculature through a percutaneous puncture site and subsequently advanced transluminally through the venous vasculature to the desired location within the vein. Alternatively, the blocker delivery catheter may be a relatively short catheter (e.g., 5–20 cm in length) that is inserted will into the vein through a small incision or opening created in the vein during a surgical procedure. The same small incision or opening may subsequently be used for attachment all of the arterial blood containing conduit to the vein in accordance with Step (a) of the above-summarized method. The radially expandable lumen blocking device may comprise a generally cylindrical frame that is compressible to a radially compact configuration of a first diameter and is subsequently transitionable to a radially expanded configuration of a second diameter. A flexible or pliable cover (e.g., an obturator) is formed on at least one end of the generally cylindrical frame to block blood flow through the vein when the generally cylindrical frame is radially expanded and implanted within the vein. An opening (e.g., a small hole or slit) may be formed in the cover to permit a guidewire to pass therethrough. In this manner, the blocking device may be initially placed in its radially compact configuration and positioned within the lumen of the delivery catheter. The delivery catheter having the blocker positioned therewithin may be positioned on or advanced over a guidewire such that the guidewire passes through the opening formed in the cover of the blocker. An elongate pusher or other device is then used to expel the blocker from the distal end of the catheter. Thereafter, because the blocker is no longer constrained by the catheter, the cylindrical frame of the blocker self-expands to its radially expanded configuration and the periphery of the blocker becomes firmly coapted with the wall of the vein, thereby holding the blocker in a substantially fixed position within the vein. The guidewire may then be removed, leaving the blocker in place within the vein. Preferably the cover of the blocker is formed of a material that may be punctured or penetrated by a catheter in the event that it is subsequently desired to re-traverse the blocker for the purpose of performing an angioplasty, atherectomy or other catheter-based interventional procedure within the vein, distal to the blocker. If the blocker is re-traversed in this manner, a second blocker may subsequently be placed in the vein proximal to the first blocker, thereby serving to re-occlude the vein after the first blocker has been traversed and rendered ineffective.

Further aspects of present invention will became apparent to those of skill in the art upon reading and understanding of the following detailed description of exemplary embodiments and upon studying of the accompanying drawings in which such exemplary embodiment are shown.

BRIEF DESCRIPTION OF THE DRAWINGS

FIG. 2b is a distal end view of the blocker device of FIG. 2a.

FIG. 3b is a is a side elevational view of an introducer that may be disposed within the lumen of the percutaneous blocker delivery catheter of FIG. 3a.

FIG. 3d is a partial longitudinal sectional view of the distal end of the blocker delivery catheter/introducer combination shown in FIG. 3a, being advanced over a guidewire.

FIG. 3e is an enlarged cross sectional view through line 3e–3e of FIG. 3d.

FIG. 3f is an enlarged, longitudinal sectional view of the distal portion of the percutaneous blocker delivery catheter shown in FIGS. 3a, 3d and 3e.

FIG. 5c is a proximal in view of the device of FIG. 5a.

FIG. 5d is a longitudinal sectional view of the device of FIG. 5a.

DETAILED DESCRIPTION OF PREFERRED EMBODIMENTS

The following detailed description makes reference to the accompanying drawings wherein showings of certain exemplary embodiments of the invention are made for the limited purpose of illustrating these exemplary embodiments and not for the purpose of exhaustively illustrating all possible embodiments of the invention.

Figure 1:
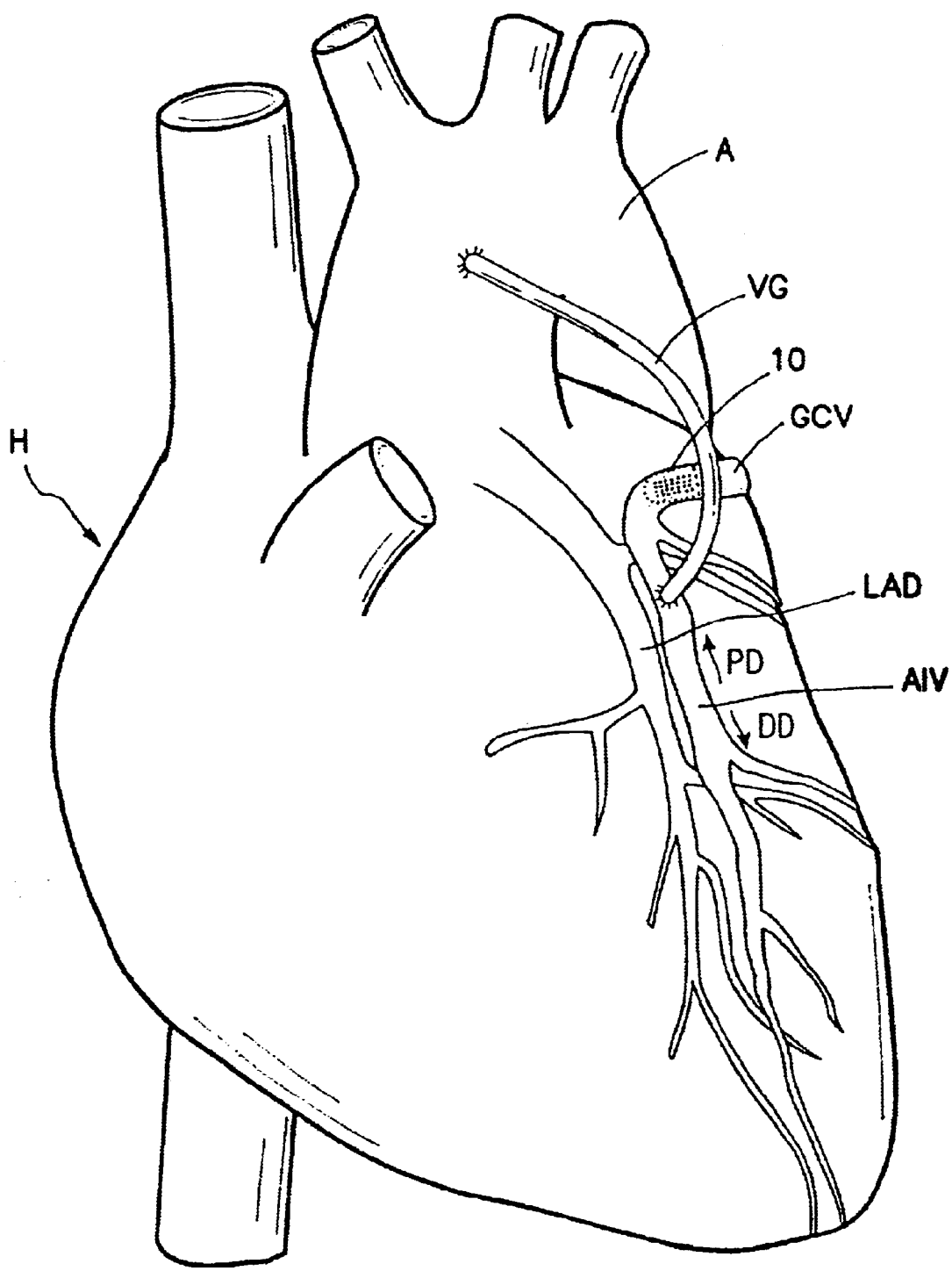
FIG. 1 is a perspective view of the human heart whereon a coronary vein bypass procedure has been performed in accordance with the present invention.

FIG. 1 generally illustrates the present invention by showing a human heart H in which one end of a vascular graft VG has been attached to the patient's aorta AO and the other end of the vascular graft has been purposely or mistakenly attached to the patient's Anterior Interventricular Vein AIV and wherein, additionally, a radially expandable vein blocking device 10 of the present invention has been surgically or percutaneously implanted in the Great Cardiac Vein GCV. The placement of the vein blocking device 10 at this location serves to prevent blood from flowing in the proximal direction PD (i.e., the direction of normal venous blood flow) through the Anterior Interventventricular Vein AIV and Great Cardiac Vein GCV, thereby eliminating the "steal" of Intraventricular Vein AIV without blocking venous outflow in the proximal direction. In this manner, the blocker 10 facilitates the desired flow of arterial blood through the Anterior Intraventricular Vein AIV in the distal direction DD (i.e., a direction opposite normal venous blood flow).

A. The Blocker Device

Figure 2A:
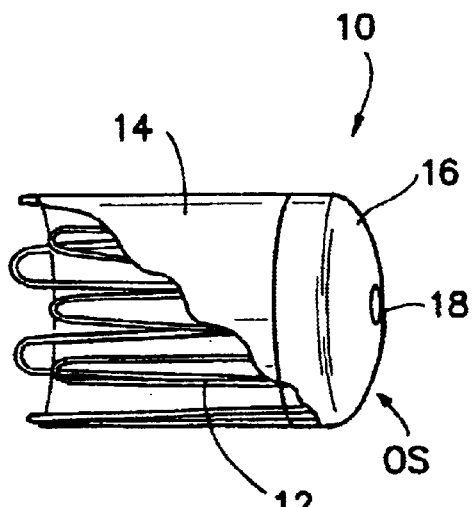
FIG. 2a is a cut-away perspective view of a radially expandable vascular blocker device of the present invention having a frame of generally zig-zag construction.
Figure 2B:
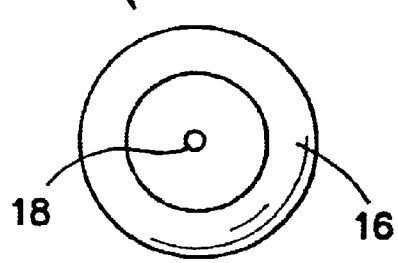

An example of a suitable vein blocking device 10 is shown in detail in FIGS. 2a and 2b. As shown, this vein blocking device 10 comprises a generally cylindrical frame 12 formed of zig-zag wire. The wire is preferably resilient or superelastic and is biased to the radially expanded configuration as shown in FIG. 2a. One example of a suitable type of wire of which the frame 12 may be formed is cardiac pacemaker lead wire formed of cobalt-stainless steel alloy. A flexible end cap 16 is formed on one end of the frame 12, as shown. This flexible end cap 16 may be formed of any suitable material, such as an elastomeric or flexible, biocompatable polymer (e.g., silicone). Optionally, a flexible cylindrical cover 14 may also be formed around the frame 12. This optional cylindrical cover 14 may be formed of any suitable material, such as woven polyester, polytetrafluroethylene, silicone, etc.

The end cap 16 may include an opening 18 to facilitate over-the-wire placement of the blocker 10 and/or to allow a controlled amount of bloodflow therethrough. This opening 18 may be a hole, slit or other suitable aperture. For applications where the opening 18 is intended to allow passage of a guidewire therethrough but to prevent passage of blood therethrough following implantation, the opening 18 will be preferably 0.2–1.0 mm in diameter or maximum cross-dimension. For other applications where the opening 18 is intended to allow passage of a guidewire therethrough and to allow some controlled amount of blood flow therethrough following implantation, the opening 18 will be preferably greater than 1.0 mm but sufficiently smaller than the diameter of the vein lumen to prevent clinically significant arterio-venous steal from occurring.

In many applications it will be preferred, but not required, for the blocker 10 to the placed within a blood vessel such that the arterial blood flow is directed against the outer surface OS of the end cap 16.

In some embodiments, an end cap 16 may be mounted on both ends of the frame 12, instead of only on one end as in the embodiment of the blocker 10 shown in the drawings. The provision of an end cap 16 on both ends of the blocker 10 will eliminate any need for selecting a particular end vs. end orientation of the blocker, and may in some cases serve to deter or prevent the exposed end of the wire frame 12 from causing trauma to or perforating the vessel wall.

Figure 2C:
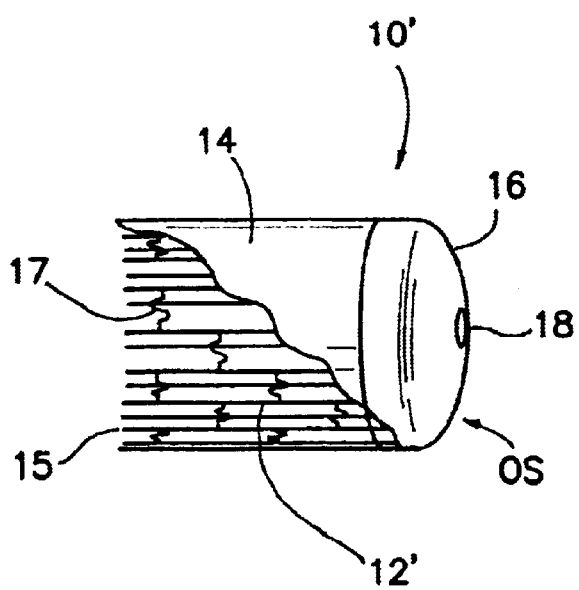
FIG. 2c is a cut-away perspective view of an embodiment of a radially expandable vascular blocker device of the present invention having a frame of non-zig-zag construction.
Figure 2D:
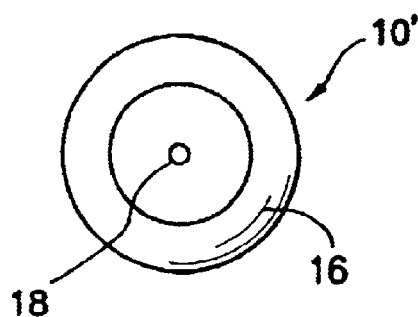
FIG. 2d is a distal end view of the blocker device of FIG. 2c.
Figure 3A:
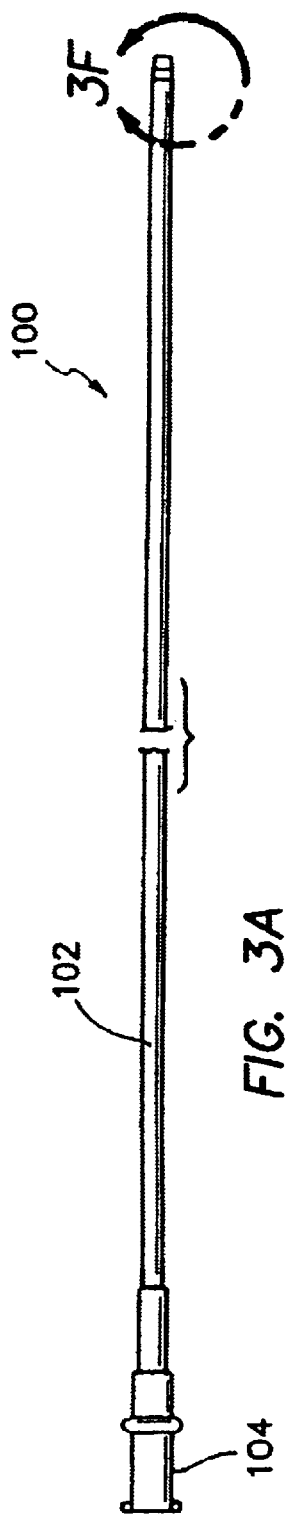
FIG. 3a is a side elevational view of a blocker delivery catheter useable for percutaneous delivery of a venous blocker apparatus in accordance with the present invention.
Figure 3B:
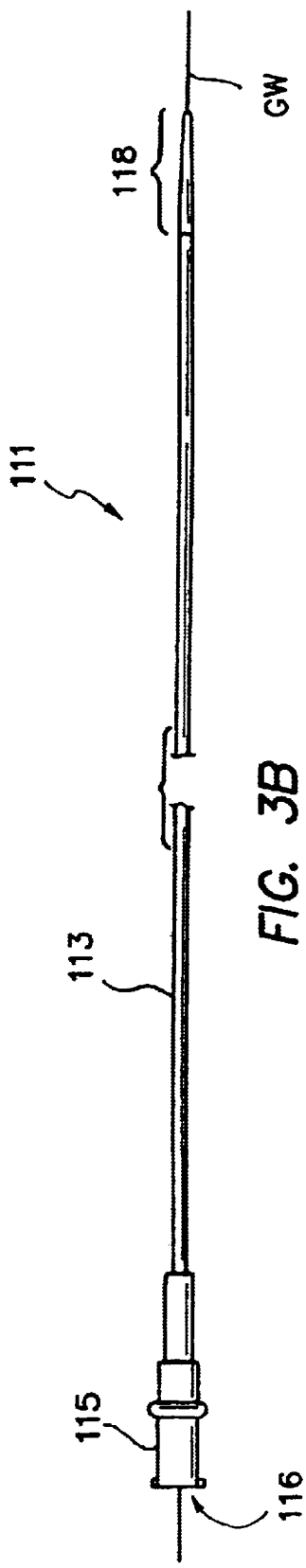
Figure 3C:
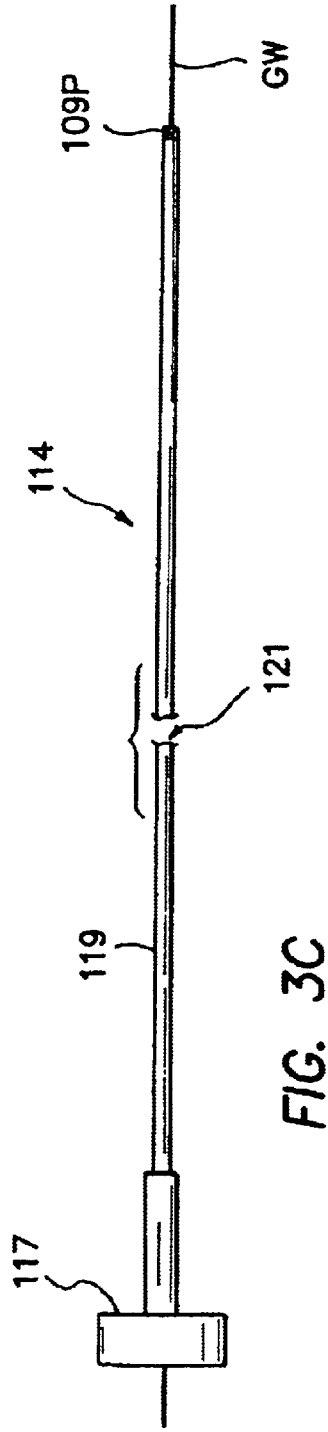
FIG. 3c is a side elevational view of a pusher that is advanceable through the percutaneous blocker delivery catheter of FIG. 3a, after the dilator has been removed from the lumen of the delivery catheter.

In the particular embodiment shown in FIGS. 2a and 2b, the wire frame 12 is bent into a series of straight segments in zig-zag construction. It will be appreciated, however, that wire frames of various other configurations may also be used. One example of a blocker device 10' having an alternative frame 12' of non-zig-zag configuration is shown in FIG. 2c. This alternative frame 12' comprises a cylindrical array of substantially straight elongate members 15 in substantially parallel relationship to one another. The elongate members 12' are interconnected and held in the substantially cylindrical array by link members 17. Each link member 17 is biased to an extended configuration whereby the frame 12' will assume its radially expanded configuration as shown in FIG. 2c. When the frame 12' is compressed to its radially compact configuration, the link members will deform or shorten, thereby allowing the straight elongate members 15 to become more closely spaced and compact in a relatively small diameter cylinder. When the frame 12' is unconstrained, the link members 17 will resiliently return to their extended configurations, thereby causing the straight elongate members 15 to become more distantly spaced apart and to form a cylinder of relatively large diameter (e.g., the diameter of the frame when unconstrained should be slightly larger than the diameter of the vein lumen into which the device 10' is to be implanted so as to result in firm coaptation or engagement of the device 10' with the surrounding vein wall). In either embodiment of this device 10,10' it is desirable that the end cover 16 and side cover 14 (if used) be securely affixed to or formed on the frame 12 or 12' to prevent separation of the end cover 16 or side cover 14 from the frame 12 or 12'.

As explained in detail herebelow, the blocker device 10 of the present intention may be implanted into the target vein using either a long catheter for percutaneous, transluminal delivery as shown in FIGS. 3a–3f and 6a–6j or a short catheter for direct surgical delivery as shown in FIGS. 4a–4b and 7a–7g.

B. Catheter System for Percutaneous Blocker Delivery

With reference to FIGS. 3a–3f, a presently preferred system for percutaneous, transluminal delivery of the blocker device 10 generally comprises a percutaneous delivery catheter 100, a tapered introducer 111, and a pusher 114.

The percutaneous delivery catheter 100 comprises a flexible, tubular catheter body 102 having a proximal Luer hub 104 and a lumen 106 extending longitudinally therethrough. A lubricious coating or lubricious liner may be the disposed on or within the wall of the lumen 106 to facilitate smooth movement of the blocker device 10 within the lumen 106. An optional braid 108 may be formed within the catheter body 102 to prevent kinking and to improve torque strength. Also, the catheter body 102 may have different stiffnesses along its length to accomplish multiple functions such as navigation of the anatomy, support of blocker delivery once in place, etc. Additionally, the catheter body 102 may be formed of radiopaque material or one or more radiopaque markers 109 may be located on the catheter body 102 to facilitate visualization of the catheter body 102 by x-ray, fluoroscopy, etc. and/or to provide a measurement of distance to the catheter tip.

The introducer 111 comprises an elongate, flexible body 113 having a guidewire lumen 116 extending longitudinally therethrough and a hub 115 formed on its proximal end. A distal portion 118 of the introducer body 113 is tapered to facilitate its advancement through tortuous or narrowed blood vessels. The introducer 111 is slightly longer than the catheter such that when the introducer 111 is fully inserted into the lumen 106 of the catheter such that its introducer hub 115 is bottomed out against the catheter hub 104, the tapered distal portion 118 of the introducer 111 will protrude out of and beyond the distal end of the catheter body 102. The introducer 112 may be radiopaque or one or more radiopaque markers may be formed on the introducer 112, to facilitate imaging of the introducer 112 by fluoroscopy, x-ray, etc.

The percutaneous delivery catheter 100 is typically 40 to 125 cm in length and its reinforcement braid (if present) preferably terminates distally at 0.1–1.0 centimeter from the distal end of the catheter body 102. A gradual taper 110 is formed about the distal end of the catheter body 102 such that the distal end of the catheter body 102 tapers to a flush transition with the outer surface of the protruding distal portion 118 of the introducer 111, as shown in FIG. 3d. The catheter lumen 106 has an inner diameter D1 which is substantially the same as the outer diameter of the introducer 111. Thus, the introducer fits snugly in the catheter lumen 106. The introducer's guidewire lumen 116 extends longitudinally through the introducer hub 115 and body 113 to permit the delivery catheter 100/introducer 111 combination to be advanced over a previously inserted guidewire GW (e.g., a 0.035 inch guidewire). The lubricious liner or coating may be disposed within or on the wall of the introducer's lumen 116 to facilitate smooth advancement of the introducer 111 over a guidewire.

The pusher 114 comprises an elongate flexible shaft 119 which may have an optional guidewire lumen 121 extending longitudinally therethrough for over-the-wire blocker delivery. A handle or hub 117 is formed on the proximal end of the pusher. The outer diameter of the pusher shaft 119 is just slightly smaller than the inner diameter of the catheter lumen 106. In this manner, after the introducer 111 has been removed and a blocker 10 has been introduced into the lumen 106 of the catheter 100, the pusher 114 may be advanced over the guidewire GW, and through the lumen 106 of the catheter 100. The pusher 114 may be radiopaque or one or more radiopaque markers may be formed on the pusher 114, to facilitate imaging of the pusher 114 by fluoroscopy, x-ray, etc.

As explained in more detail in the operational example set forth herebelow, after the catheter 100 and introducer 111 have been advanced over the guidewire GW, the introducer 111 is withdrawn and removed. Thereafter, for over-the-wire delivery, the proximal end of the guidewire GW is inserted through the aperture 18 formed in the end cap 16 of a blocker device 10 and the blocker 10 is then collapsed to its radially compact configuration. The collapsed blocker 10 is then advanced over the guidewire into the lumen 106 of the catheter 100. A pusher 114 having an optional guidewire passage lumen 121 is then advanced over the guidewire GW and into the catheter lumen 106 until the distal end of the pusher body 116 contacts the blocker device 10. The pusher body 116 is then advanced in the distal direction until the radially collapsed blocker 10 has been pushed to a position at or near the distal end of the catheter 100. The pusher body 1 16 is then advanced and/or the catheter 100 is withdrawn, to cause the blocker 10 to be expelled out of the distal end of the catheter 100.

For non-over the wire blocker delivery, essentially the same procedure is used, except that the guidewire GW will be extracted and removed before the blocker 10 is introduced into the catheter lumen 106 and neither the blocker 10 nor the pusher 114 will be required to have a lumen for guidewire passage. Even though no guidewire passage through the blocker 10 is required in non-over-the-wire blocker deliveries, in cases where it is desired for the blocker 10 to effect less than total blockage of the vein lumen, one or more openings of more than 1 mm in diameter or cross dimension may still be present in the blocker end cap 16 to allow a controlled amount of blood flow therethrough.

Although FIGS. 3a–3f show an over-the-wire catheter system, it will be appreciated that an offset or "monorail" guidewire lumen may alternatively be formed on the catheter body, thereby eliminating the need for the central guidewire lumen 116 in the introducer 111, the provision of any guidewire lumen in the pusher body 116 and the need for any hole 18 in the end cap 16 of the blocker 10.

Catheter System for Blocker Delivery Via a Venotomy

Figure 4A:
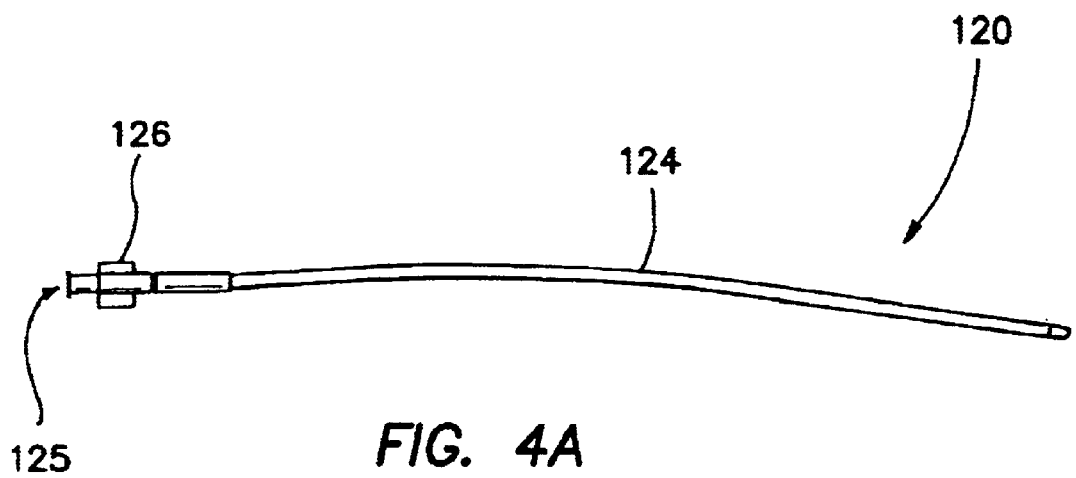
FIG. 4a is a perspective view of a blocker delivery catheter that is useable for insertion into a vein through an incision or opening formed in the vein during an open or minimally invasive surgical procedure and useable for delivering a radially expandable venous blocking device into the vein in accordance with the present invention.
Figure 4B:
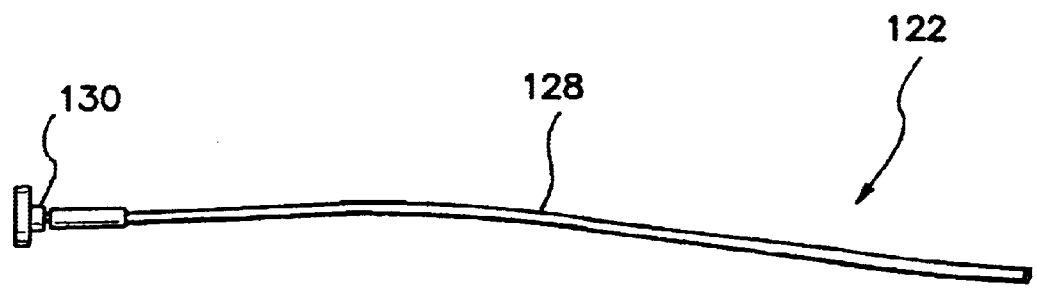
FIG. 4b is a perspective view of a pusher apparatus that is advanceable through the lumen of the blocker delivery catheter of FIG. 4a to expel a radially expandable blocker device therefrom.

FIGS. 4a and 4b show another catheter system that is usable for delivering a blocker 10 into the lumen of a vein through a venotomy (i.e., an incision or opening formed in a vein) created during the performance of an open or minimally invasive surgical procedure (e.g., a surgical or thoracoscopic CVBG operation). This system comprises a venotomy delivery catheter 120 and an accompanying pusher 122. The venotomy delivery catheter 120 comprises an elongate flexible catheter body 124 that is constructed substantially the same as the above-described percutaneous delivery catheter body 102, except that it need not include a tapered distal tip 110 as it is not intended for use with an introducer. A Luer hub 126 is formed on the proximal end of the venotomy catheter body 124. Because the venotomy delivery catheter 120 is inserted only a short distance into a vein, it need not be as lengthy as the percutaneous delivery catheter 100.

Rather, venotomy delivery catheter 120 is typically no more than 5 to 20 cm in length.

The accompanying pusher 122 comprises and elongate, flexible shaft 128 having a handle 130 formed on its proximal end. The pusher shaft 128 is approximately the same length as the venotomy delivery catheter body 124. This pusher 122 may be of solid construction and devoid of any lumen, as it is not intended for advancement over a guidewire. When the pusher 122 is advanced through the lumen in the catheter 120 until the handle or hub 130 of the pusher 122 becomes bottomed out against the lure hub 126 of the catheter 120, the distal end of the pusher body 128 may be flush with or only slightly proximal to the distal end of the catheter body 124.

Those of skill in the art will recognize that the venotomy delivery catheter 120 may, in at least some applications, be used with a stylet or introducer (not shown) similar to the introducer 111 described hereabove in connection with the percutaneous delivery catheter 100. Such stylet or introducer may further be provided with a guidewire lumen to allow for over-the-wire insertion of the catheter 120 in cases where such over-the-wire technique is desired. Also, a blocker 10 having a opening 18 (e.g., a hole or slit) in its end cap 16 may be used when it is desired to actually advance and deploy the blocker 10 itself using an over-the-wire technique. The manner in which this venotomy delivery catheter system is used to deliver a blocker 10 is described in detail herebelow in relation to the example shown in FIGS. 7a–7g.

D. Device for Introducing Blocker Into Catheter

Although a blocker 10 could be pre-loaded into the lumen of the venotomy delivery catheter 120, by the manufacturer, it may be undesirable to do so as maintaining of the blocker 10 in a radially collapsed configuration for a long period of time could result in less than full radial expansion of the blocker 10 when it is subsequently implanted in the vein. On the other hand, it may not be feasible to pre-loaded the blocker 10 into the lumen of the percutaneous delivery catheter 100, especially for use in applications where the catheter 100 is employed in conjunction with the introducer 111, as the blocker 10 will be precluded from occupying the lumen 106 of the percutaneous delivery catheter 100 until such time as the introducer 111 has been removed therefrom. Accordingly, it may be desirable for the blocker to be radially collapsed and introduced into the percutaneous delivery catheter 100 or the venotomy delivery catheter 120 during or immediately prior to the operative procedure. In view of this, the present invention includes a blocker introduction device 200 that is usable to radially collapse the blocker 10 and to introduce the blocker 10 to either the percutaneous delivery catheter 100 or the venotomy delivery catheter 120.

As shown in FIGS. 5a–5d, the blocker introduction device 200 comprises a rigid plastic body 202 having a lumen 204 extending longitudinally therethrough. A funnel or tapered region 206 is formed at the proximal end of the lumen 204. A male Luer connector 210 with an internally threaded, rotatable sleeve 208 is formed on the distal portion of the rigid plastic body 202.

In operation, the male Luer connector 210 is inserted into the female Luer hub 104 of the percutaneous delivery catheter 100 or the female Luer hub 126 of the venotomy delivery catheter 120, and the sleeve 208 is then rotated in the clockwise direction such that the internal threads of the sleeve 208 engage the flange of the female Luer hub 104 or 126, thereby firmly attaching the blocker introduction device 200 to the proximal end of the delivery catheter 100 or 120. The radially expandable blocker device 10 is radially compressed and advanced into the tapered proximal portion 206 of the lumen 204 of the blocker introduction device 200. In cases where over the wire blocker delivery is to be accomplished, a guidewire will protrude out of the distal end of the blocker introduction device 200, the proximal end of that guidewire will be passed through an optional opening 18 formed in the blocker end cap 16. In applications where non-over-the-wire blocker delivery is intended, the guidewire will be extracted and removed before the blocker introduction device 200 is attached to the proximal end of the catheter 100.

Figure 5A:
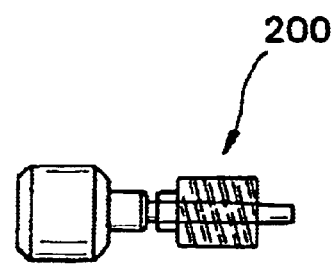
FIG. 5a is a side elevational view of an introducer device that is useable for compressing a radially expandable implantable device and introducing such device into the lumen of a delivery catheter.
Figure 5B:
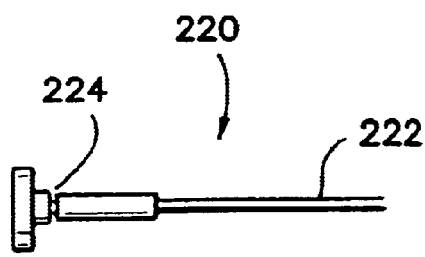
FIG. 5b is a side elevational view of a pusher that is useable for pushing a radially compressed implantable device through the introducer of FIG. 5a and into the lumen of a delivery catheter.
Figure 5C:
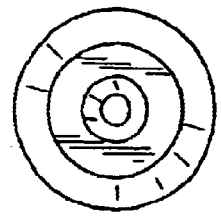
Figure 5D:
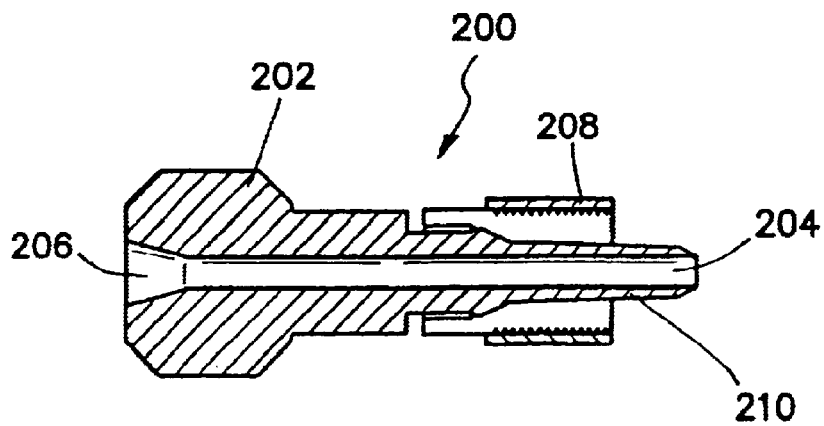

A small pusher 220 as shown in FIG. 5b comprises a flexible shaft 222 having a handle 224 formed on the proximal end thereof. The distal end of the pusher shaft 222 is then inserted into the proximal end of the lumen 204 of the blocker introduction device 200 and the pusher 220 is advanced in the distal direction to push the blocker 10 fully into the nontapered portion of the lumen 204. At this point, and the blocker will have been fully compressed to its radially collapsed configuration. Thereafter, when it is desired to load the blocker 10 into the lumen of the delivery catheter 100 or 120, the small pusher 220 will be further advanced in the distal direction until its handle 224 bottoms out against the proximal end of the rigid body portion 202 of the blocker introduction device 200. At this point, the distal end of the pusher shaft 222 will be substantially coterminal with, or proximal to, the distal end of the introduction device's lumen 204 and the blocker 10 will have been thereby advanced into a position within the lumen 106 of the percutaneous blocker delivery catheter 100 or the lumen (not shown) of the venotomy blocker delivery catheter 120. In cases where over-the-wire blocker delivery is to be accomplished the small pusher 220 may have a lumen extending longitudinally therethrough and the proximal end of the guidewire may be intorduced into the distal end of the pusher shaft 222 such that the pusher 220 will be advanced over-the-wire. Alternatively, the pusher shaft 222 may be small enough in size to be inserted next to a guidewire while pushing the blocker 10 over-the-wire. In applications where non-over-the-wire blocker delivery is intended, the pusher shaft 222 may be solid (i.e., devoid of a longitudinally extending lumen) and just slightly smaller in diameter than the inner diameter of the inner bore of the blocker introduction device 200.

E. Method for Percutaneous Blocker Delivery in Conjunction With Intentional of Inadvertent CVBG FIGS. 6a–6j show the triangle of Brock-Moscheau (a name given to the configurational and spatial relationship between certain arteries and veins of the human heart) of the heart of a human patient. These figures illustrate, in step-by-step fashion, a method for using the percutaneous blocker delivery catheter system of FIGS. 3a–3f to deliver a blocker device 10 into a coronary vein in conjunction with a surgical CVBG procedure.

Figure 6A:
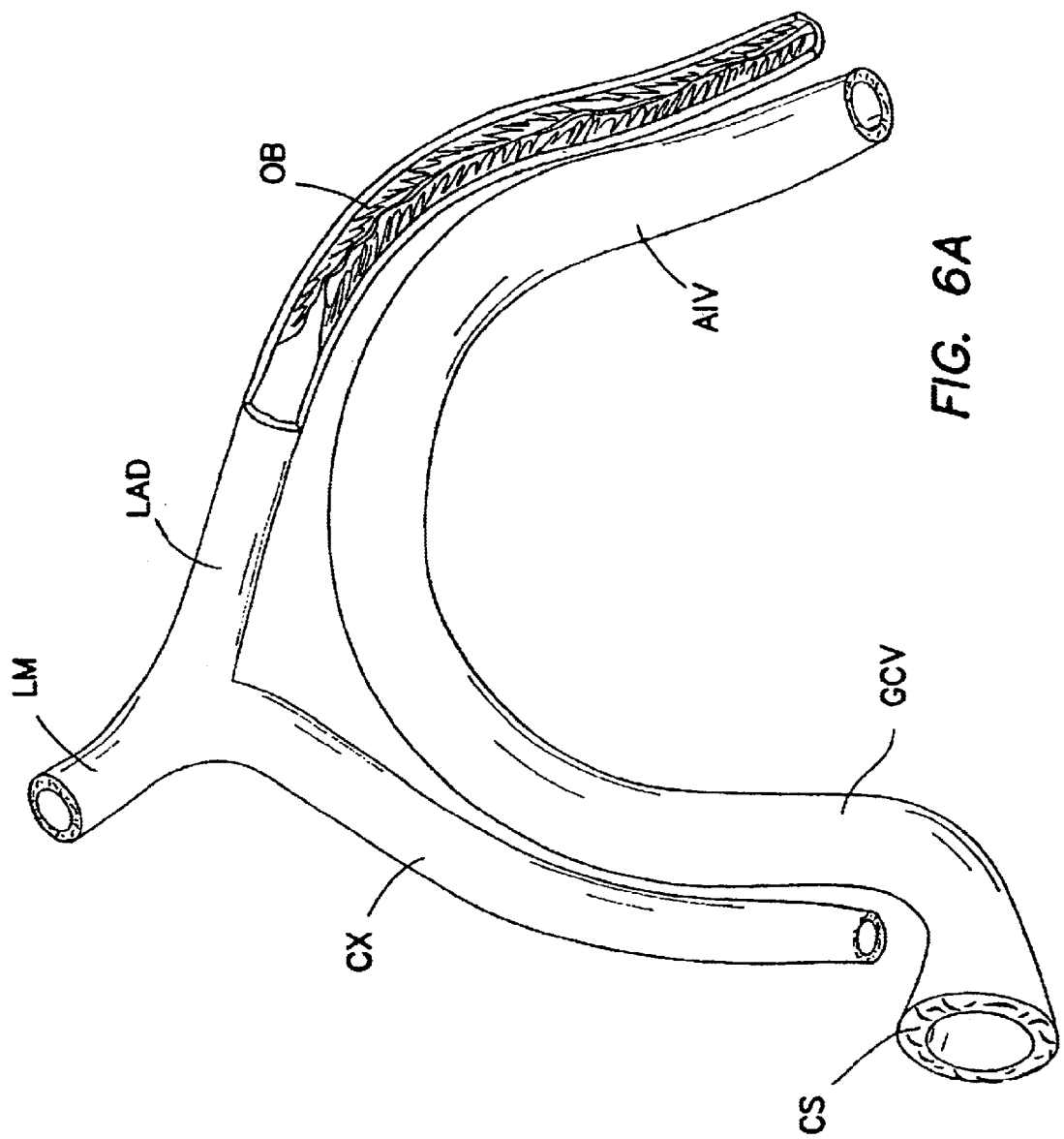
FIGS. 6a–6j show, in stepwise fashion, a percutaneous, transluminal method for blocking blood flow through a vein into which arterial blood has been caused to flow in accordance with the present invention.

As shown in FIG. 6a, the left main coronary artery LM bifurcates to form the circumflex CX and left anterior descending LAD coronary arteries. A portion of the left anterior descending coronary artery LAD is shown in cut-away format, revealing a large diffuse obstruction OB within that artery. The obstruction OB is formed of atherosclerotic plaque and constitutes a near total occlusion of the artery LAD. The obstruction OB extends distally within the left anterior descending artery LAD such that no patent distal portion of that artery is available for traditional coronary artery bypass grafting. In view of the existence of this diffuse obstruction OB of the left anterior descending artery LAD, this patient is identified as a candidate for a coronary venous bypass graft procedure CVBG with percutaneous delivery of a blocker 10 into the great cardiac vein GCV, in accordance with the present invention.

A general anesthetic is administered to the patient and surgical access to the heart is gained by either an open thoracotomy (e.g., a median sternotomy) or by forming a plurality of minimal access incisions (e.g., small 2–5 cm incisions) in the patient's chest and inserting a thoracoscope through one of the minimal access incisions in accordance with known thoracoscopic cardiac surgical technique (sometimes referred to as either "port access coronary artery bypass (PORTCAB)" or minimally invasive direct coronary artery bypass (MIDCAB)"). In some cases, the heart will be stopped and the patient will be placed on cardiopulmonary bypass. In other cases, the procedure may be performed on the beating heart, without cardiopulmonary bypass, in accordance with the currently known or hereafter devised techniques for such "beating heart" or "off-pump" cardiac surgery.

Figure 6B:
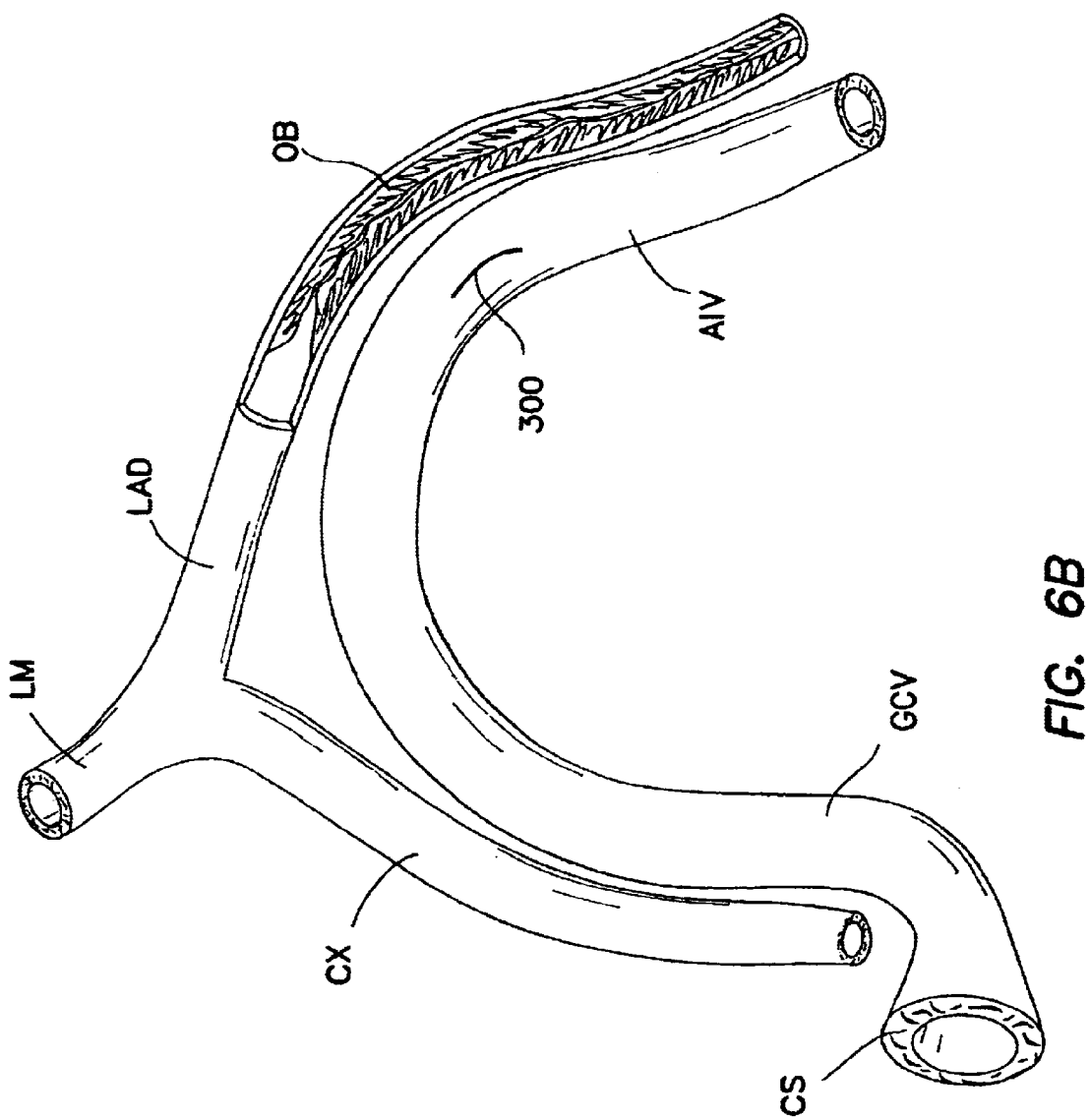

As shown in FIG. 6b, a small venotomy incision 300 is formed in the epicardial aspect of the anterior interventricular vein AIV. In cases were the patient's heart has been stopped and the patient has been placed on cardiopulmonary bypass, there will be little or no blood flow through the coronary veins and thus there will be no need for local hemostasis during or after creation of the venotomy incision 300. However, in cases where the procedure is performed on a beating heart, it will be desirable to compress or occlude the anterior interventricular vein AIV at a location distal to the site of the venotomy incision 300 to prevent blood from being lost through the venotomy incision 300. Examples of commercially available devices that are usable for this purpose include the Myoclude Coronary Occlusion Clip Kit available from U.S. Surgical, Inc., Norwalk, Conn. and the CTS Flowcoil Shunt available from Cardiothoracic Systems, Inc., Cupertino, Calif.

Figure 6C:
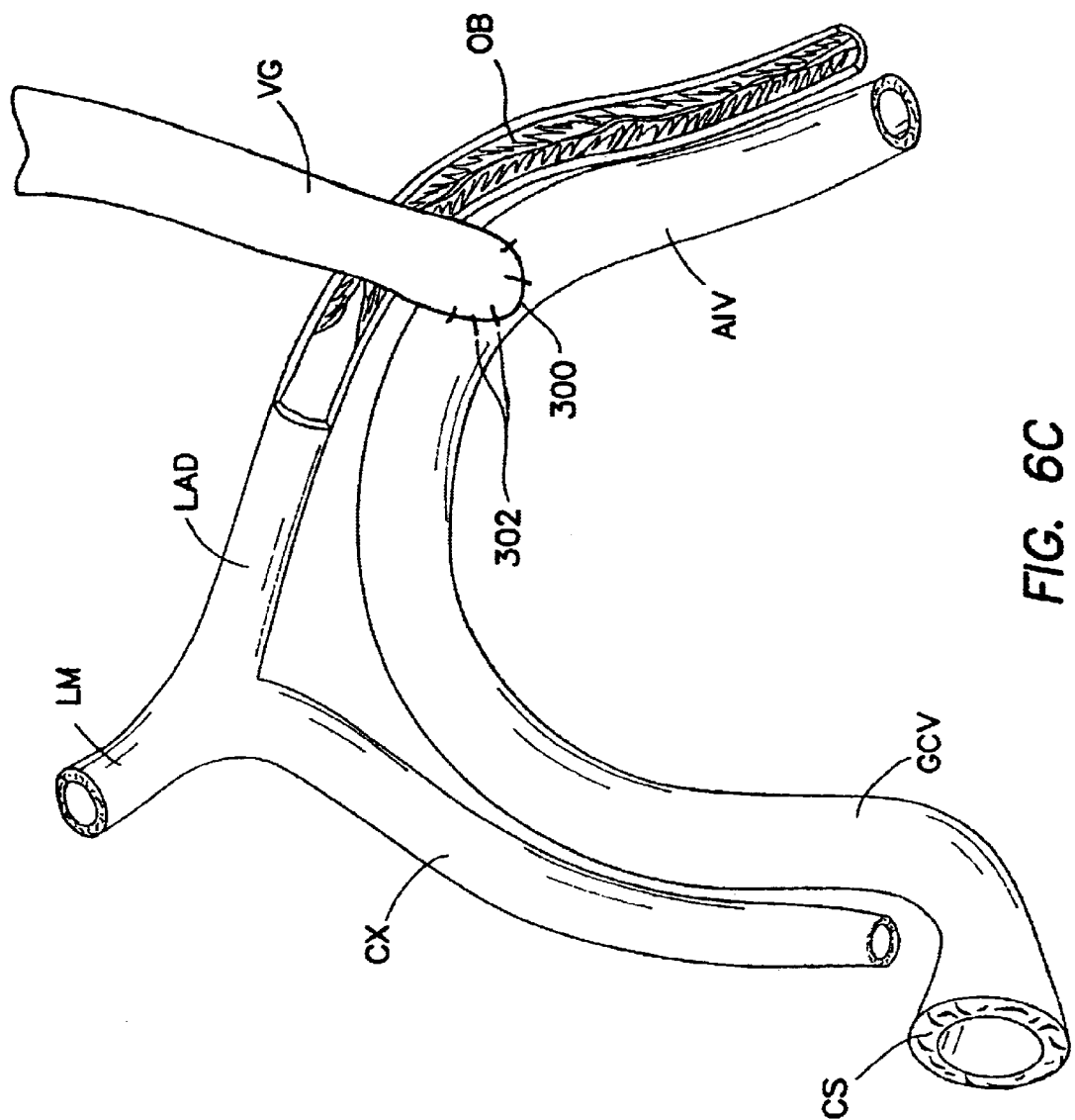

Thereafter, as shown in FIG. 6c, the free end of a vascular graft VG is attached, by end to side anastomosis 302, to the venotomy opening 300 such that arterial blood may flow through the vascular graft VG into the anterior interventricular vein AIV. Several types of vascular grafts VG suitable for this purpose are well known in the art. For example, the vascular graft VG may comprise the internal mammary artery or other suitable artery that has been transected and dissected free from its normal anatomical location within the patient's chest cavity. Alternatively, the vascular graft VG may comprise a harvested segment of blood vessel (e.g. saphenous vein) or suitable biological or synthetic tubular graft that has been connected at its other end to the patient's aorta or other arterial blood source.

Figure 6D:
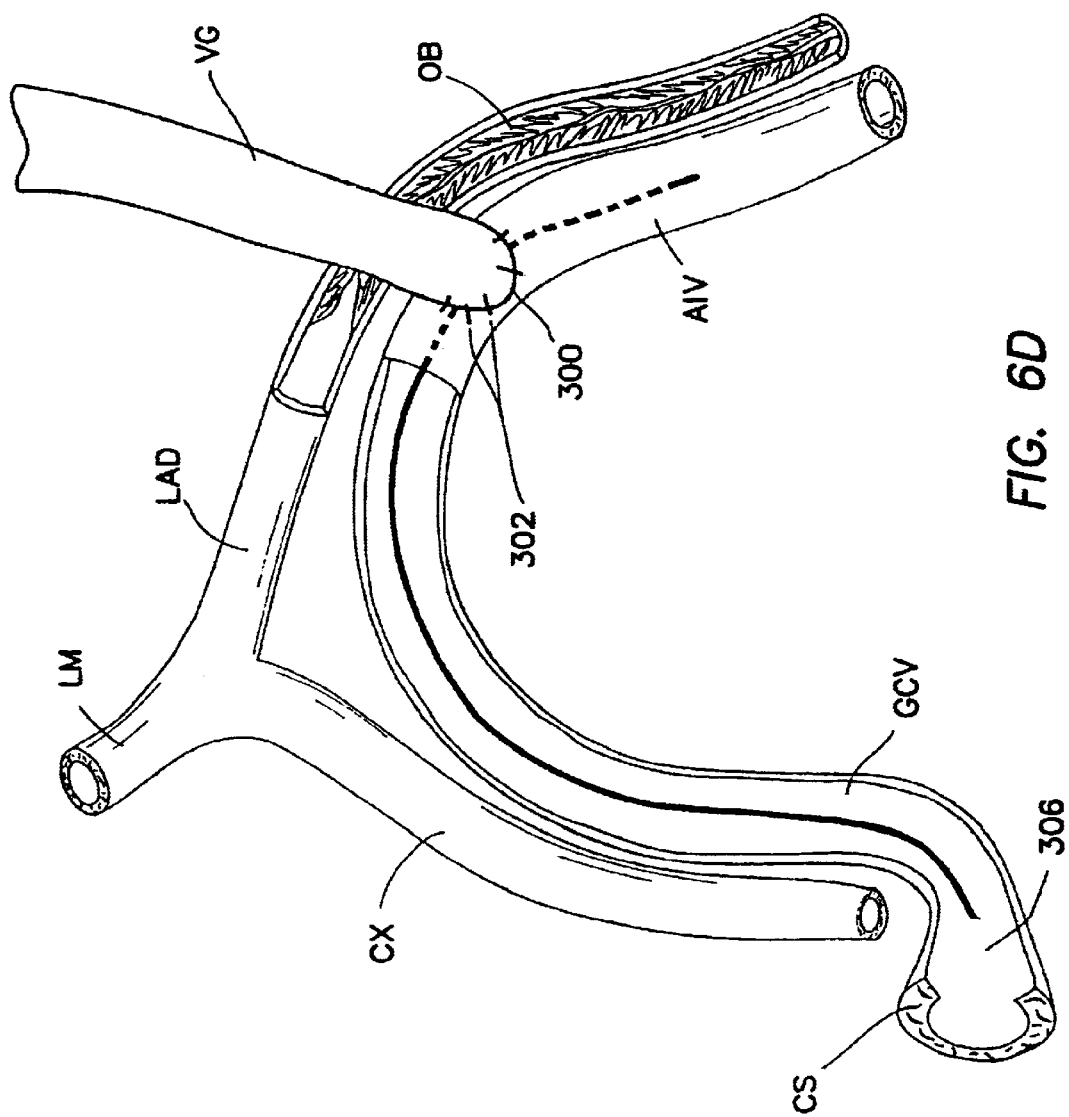
Figure 6E:
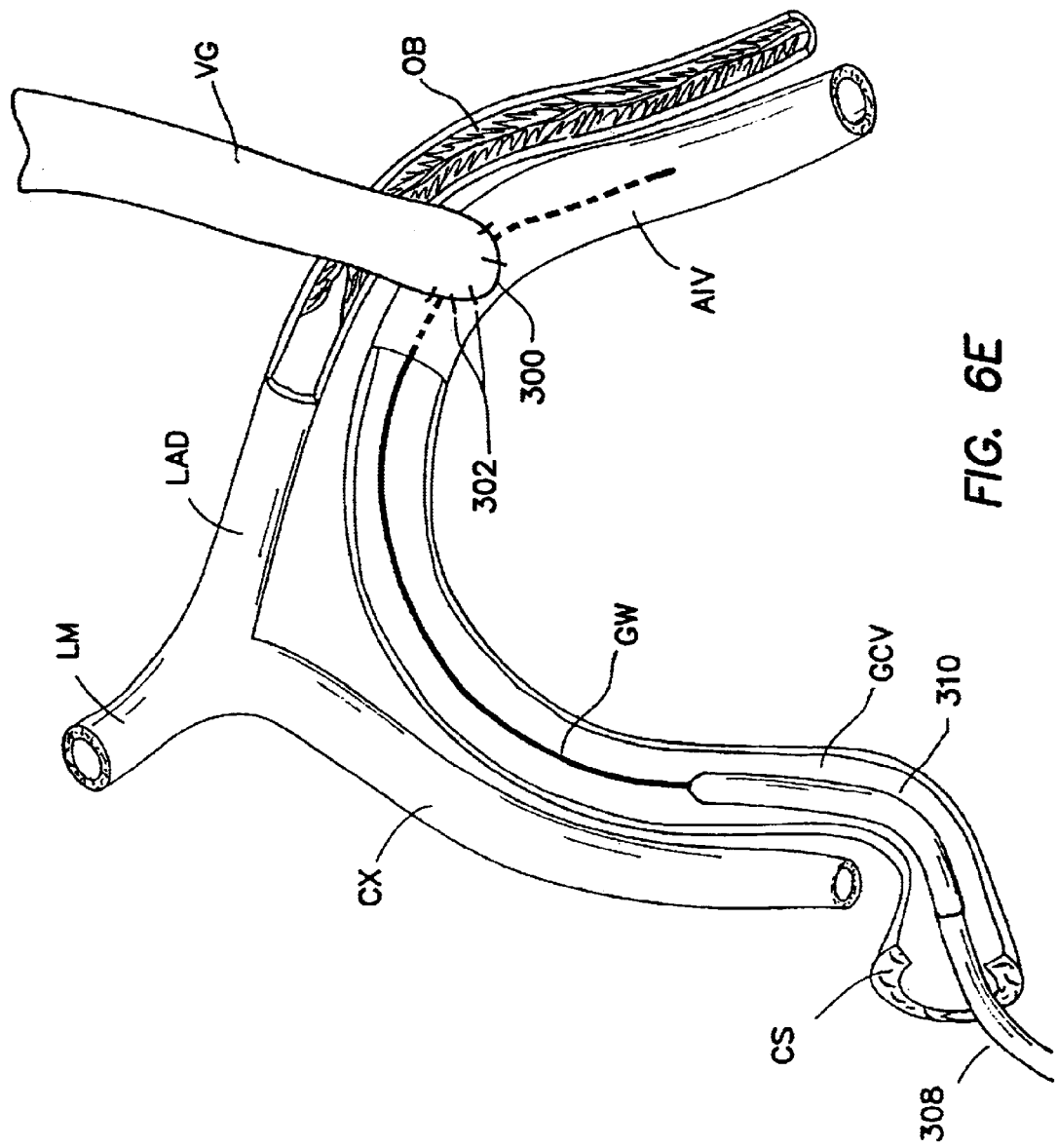
Figure 6F:
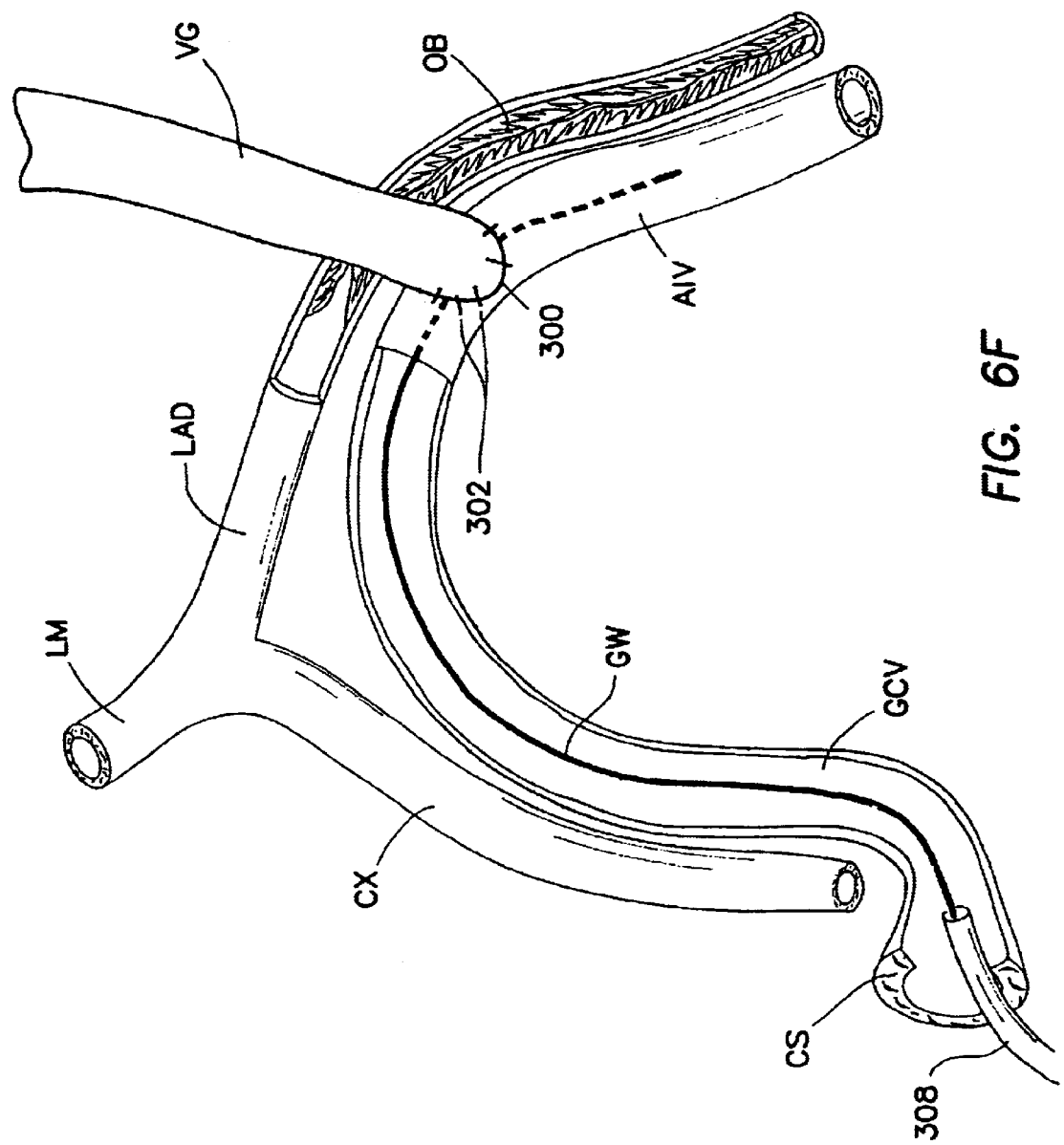

As shown in FIG. 6d, a standard angiographic catheter 306 (e.g., a modified Simmons-type angiographic catheter available from Cook Cardiology, Bloomington, Ind.) is percutaneously introduced into the patient's vasculature through a puncture site in a femoral vein or other suitable vein, and is advanced through the vasculature until the distal end of the angiographic catheter 306 is in the coronary venous sinus CS of the patient's heart. Thereafter, a guidewire (e.g., a 0.035 inch diameter guidewire) is advanced through the angiographic catheter 306, through the great cardiac vein GCV and into the anterior interventricular vein AIV, such that the distal end of the guidewire GW has traveled past the location at which the blocker 10 is to be implanted. Thereafter, as shown in FIG. 6e, the angiographic catheter 306 is removed and a coronary sinus guide catheter 308 and accompanying tapered introducer 310 are advanced over the guidewire GW until the distal end of the coronary sinus guide catheter 308 is positioned in the coronary sinus CS. One coronary sinus guide catheter 308 and accompanying introducer 310 that are usable for this purpose are described in PCT international publication WO99/49793 (Flaherty et al.) entitled Catheters, Systems and Methods for Percutaneous In Situ Arterio-Venous Bypass. Thereafter, as shown in FIG. 6f, the guide introducer 310 is extracted and removed, leaving the coronary sinus guide catheter 308 and guidewire GW in-place.

Figure 6G:
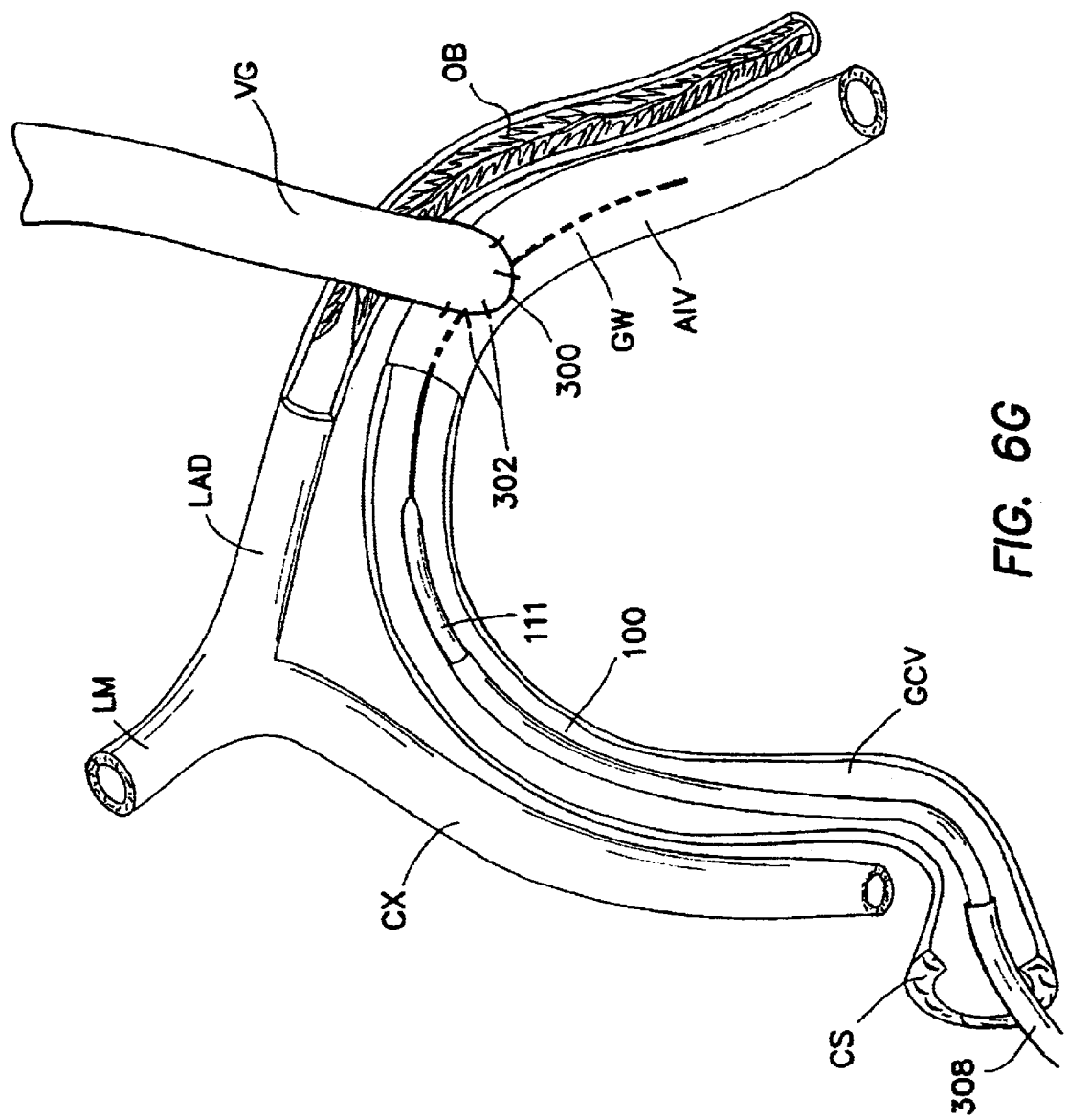

Next, as shown in FIG. 6g, the introducer 111 is inserted through the lumen 106 of the blocker delivery catheter 100 in the manner described above and shown in FIG. 3d. The proximal end of the guidewire GW is then inserted into the distal end of the introducer's guidewire lumen 116 and the blocker delivery catheter-introducer combination 100,111 is advanced over the guidewire GW, through the coronary sinus guide catheter 308 and into the great cardiac vein GCV, as shown.

Figure 6H:
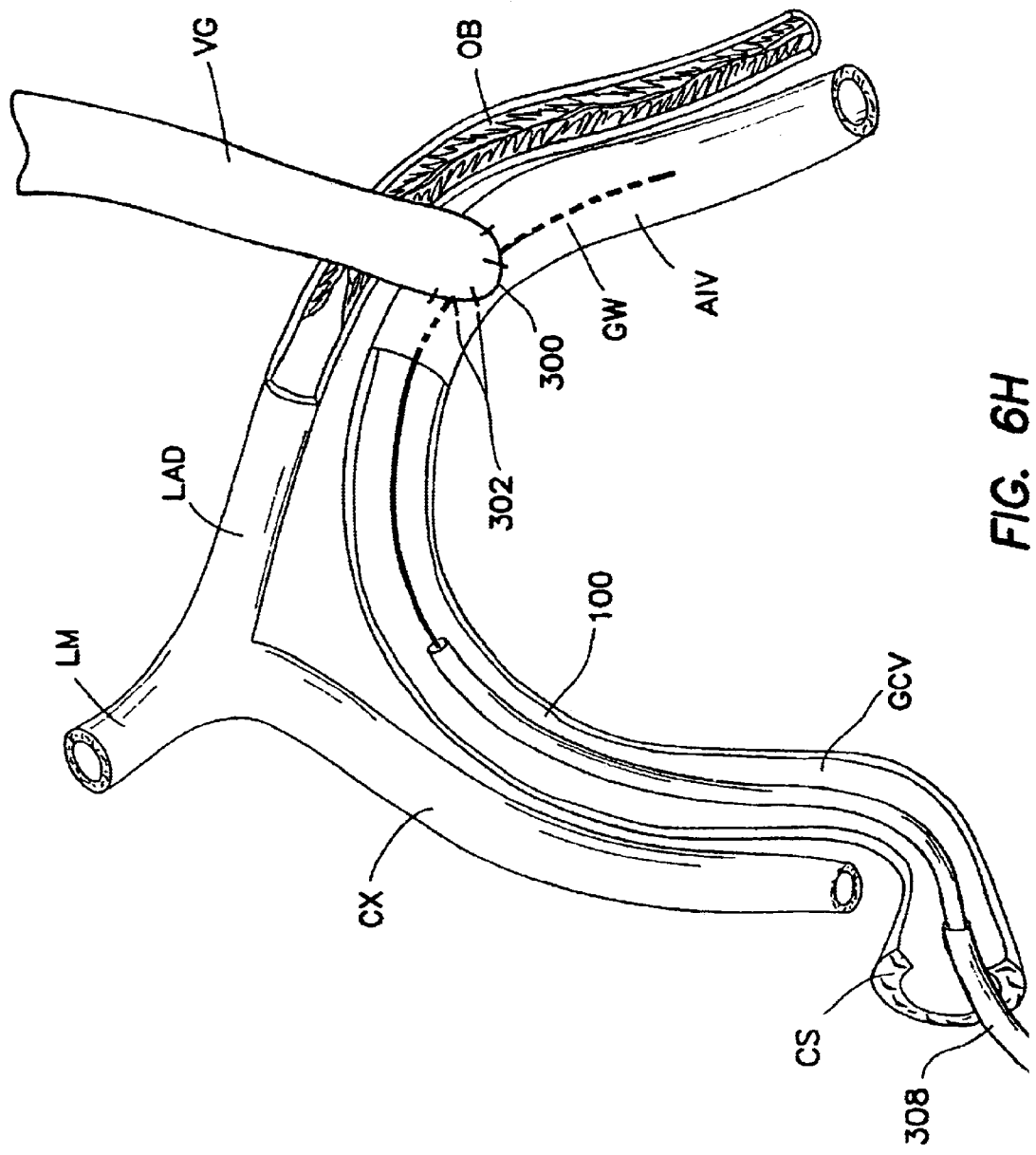

As illustrated in FIG. 6h, the introducer 111 is then extracted and removed, leaving the distal end of the blocker delivery catheter 100 positioned within the vein at the location at which the distal end of the blocker device 10 is to be positioned after implantation (e.g., near the location at which the great cardiac vein merges into the Anterior Intraventricular Vein AIV).

A blocker introduction device 200 of the type shown in FIG. 5a is then attached to be proximal Luer hub 104 of the delivery catheter 100 and a blocker 10 is introduced into the lumen 106 of the blocker delivery catheter 100 in the manner described in detail hereabove. Since the procedure illustrated in these particular figures is an over-the-wire blocker delivery, the proximal end of the guidewire GW will protrude from the proximal end of the-blocker introduction device 200, and the blocker 10 (having an opening 18 through which the guidewire GW extends) will be pushed into the catheter lumen 106 in an over-the-wire fashion, as described hereabove. The blocker introduction device 200 is then removed from the catheter 100.

Figure 6I:
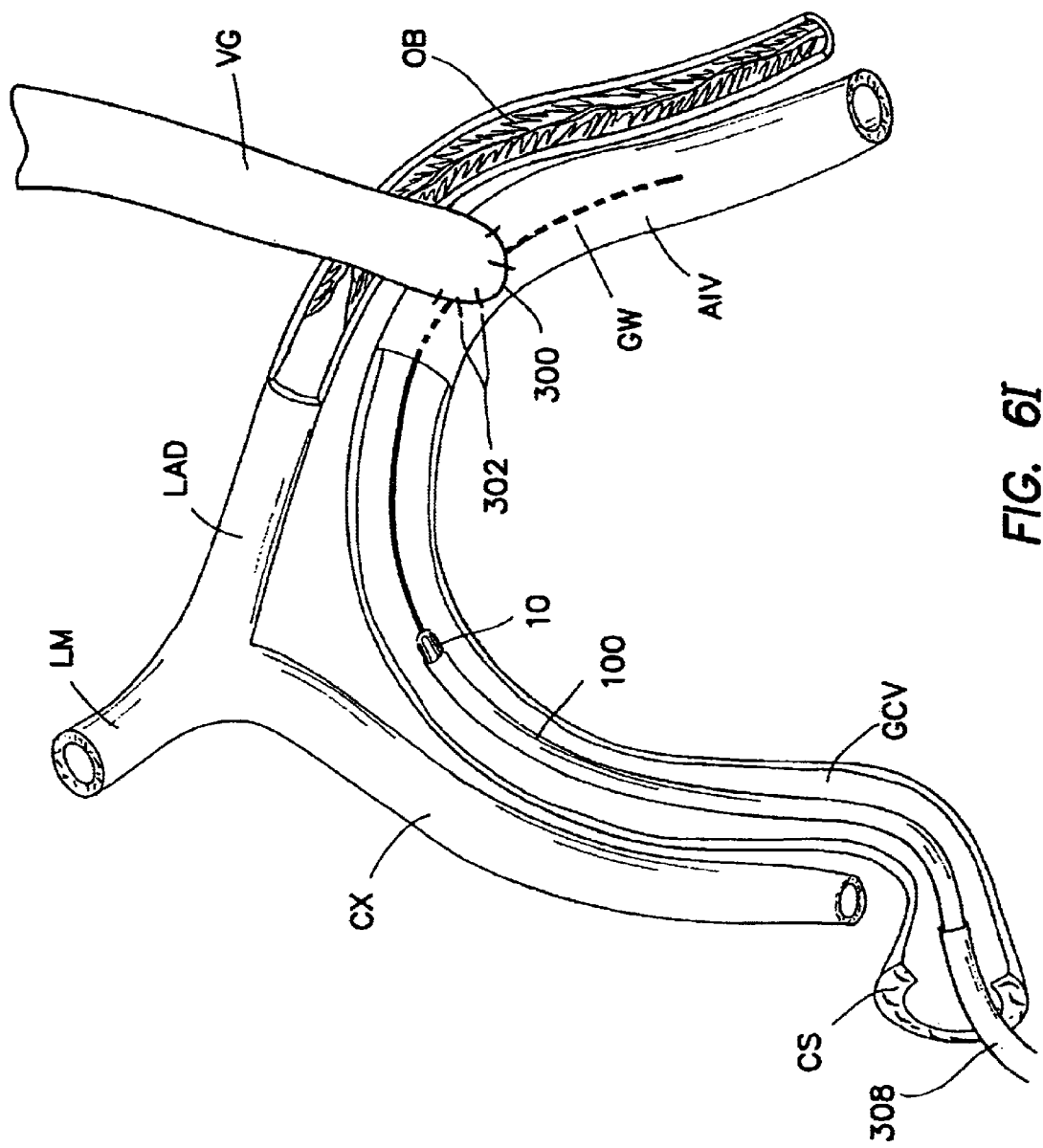
Figure 6J:
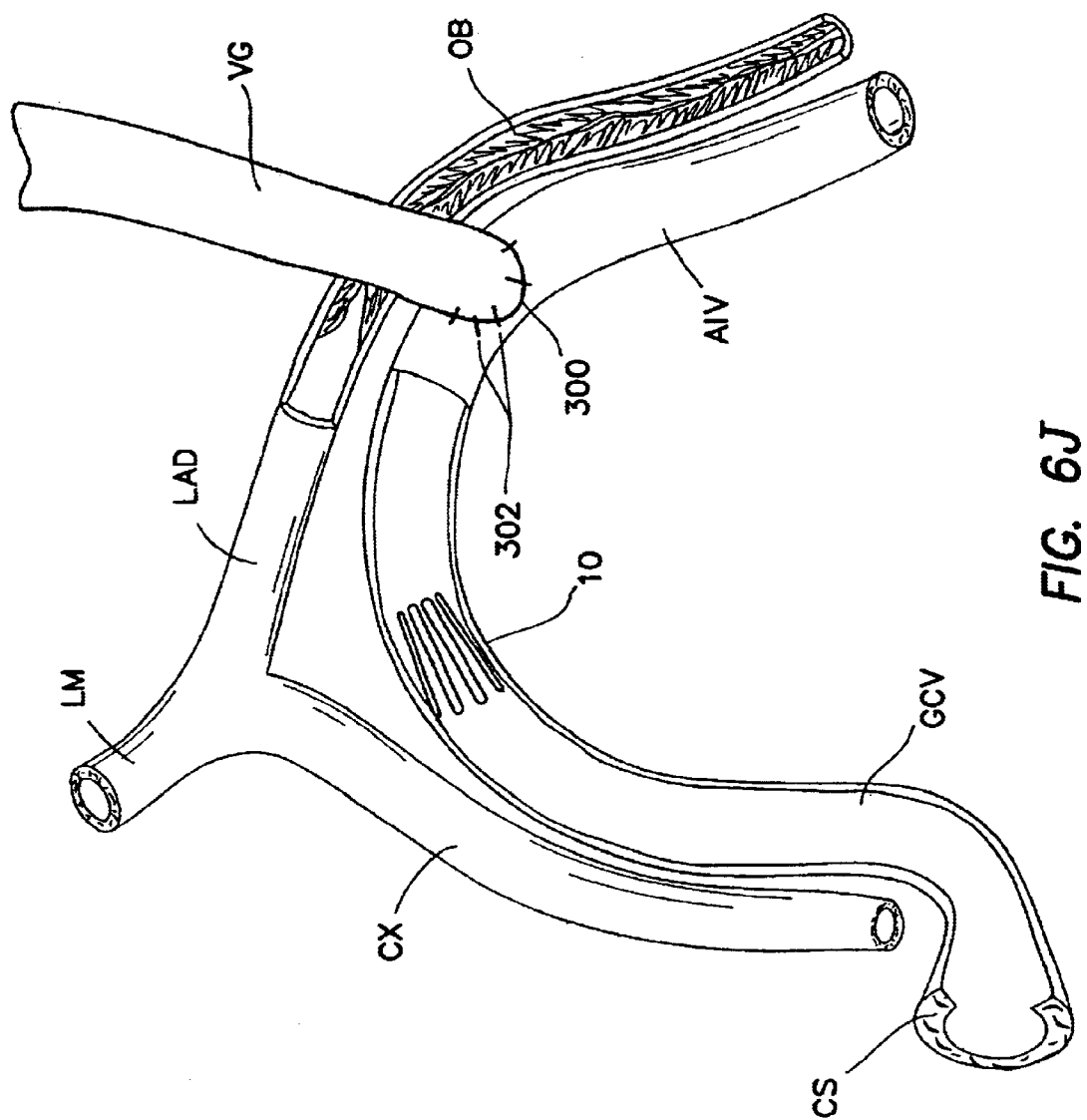

The proximal end of the guidewire GW is then inserted into the distal end of the guidewire lumen 119 that extends through the long pusher 114 and that pusher 114 is advanced over the guidewire GW and through the lumen 106 of the delivery Catheter 100, pushing the blocker as it goes, until the distal end of the blocker 10 reaches the distal end of the delivery catheter 100. Thereafter, as shown in figure 6i, the pusher 114 is held in fixed longitudinal position while the delivery catheter 100 is retracted in the proximal direction, causing the blocker 10 to be expelled out of the distal end of the delivery catheter 100. As shown in FIG. 6j, when the blocker 10 is no longer constrained by the surrounding catheter 100, the blocker will radially self-expand. The blocker is sized such that, when the blocker 10 is radially expanded, its periphery will firmly coapt with the wall of the great cardiac vein GCV and the end cap 16 of the blocker is positioned transversely across the lumen of the great cardiac vein GCV so as to block blood from flowing through the great cardiac vein GCV in the distal direction, past the blocker. The radial expansion of the blocker 10 within the lumen of the vein may be observed fluoroscopically to ensure that the blocker 10 has been fully expelled out of the distal end of the catheter 100 and has expanded into firm coaptation with the surrounding wall of the vein with the end cap of the blocker 10 extending transversely across and substantially blocking the lumen of the vein. After the expansion and implantation of the blocker 10 has been verified, the pusher 114 is withdrawn and removed.

It is preferable that the distal end of the pusher body 116 not protrude beyond the distal end of the catheter body 113 as the blocker is expelled from the end of the catheter body 113, thereby minimizing the potential for the pusher body 116 causing injury to or perforation of the blood vessel wall. Accordingly, the pusher 114 may be sized and configured relative to the delivery catheter such that, when the handle or proximal hub 117 of the pusher is in abutment with the hub 104 of the catheter 100, the distal end of the pusher body 116 will be flush with or proximal to the distal tip 110 of the catheter body 102. In order to allow for applications of the system while the catheter 10 extends through multiple curvatures of tortuous blood vessels, the pusher body 113 may actually have to be longer than the catheter body 102 in order for the distal end of the pusher to come close to or flush with the distal end of the catheter body 102 when the pusher 111 is fully advanced and its handle or hub 117 is bottomed out against the hub 104 of the catheter. The entire pusher shaft 119 may be radiopaque and/or a radiopaque marker 109p may be formed at the distal tip of the pusher body 119 to enable the operator to clearly visualize by fluoroscopy the location of the pusher's distal end to avoid inadvertent advancement of the pusher out of and beyond the distal end of the delivery catheter 100.

In this example, the blocker is shown as having been implanted with the outer surface OS of its end cap 14 directed counter to the proximally directed arterial blood flow. It will be appreciated, however, that the bocker 10 may in some applications be turned end-to-end 180 degrees such that the inner surface of the end cap 14 is directed counter to the direction of bloodflow.

Those of skill in the art will appreciate that because this method for percutaneous delivery and implantation of the blocker 10 is performed percutaneously, it may be carried out before, during or after the surgery or interventional procedure wherein the vascular graft VG is connected to the coronary vein. In this regard, in cases where a vascular graft VG is connected to a vein inadvertently (e.g., believing the vein to be an artery), it will be possible to subsequently deal with the error by percutaneously 10 implanting a blocker 10 in the affected vein when the error is discovered (e.g., often times several weeks or even months after the be vascular grafting procedure has been completed).

Additionally, those of skill in the art will appreciate that although this example has been described with reference to coronary surgery, essentially the same procedure can be performed elsewhere in the body (e.g., the brain, the leg, etc.), for the purpose of bypassing obstructed arteries that occur in those other areas of the body.

E. Method for Blocker Delivery Via Venotomy in Conjunction With Intentional or Inadvertent CVBG FIGS. 7a–7f show an example of a procedure wherein an intraluminal vein blocking device 10 of the present invention is introduced through a venotomy opening and implanted within a coronary vein, during a minimally invasive (thoracoscopic) or open surgical CVBG procedure.

Initially, a general anesthetic is administered to the patient and surgical access to the heart is gained by either an open thoracotomy (e.g., a median sternotomy) or by forming a plurality of minimal access incisions (e.g., small 2–5 cm incisions) in the patient's chest and inserting a thoracoscope through one of the minimal access incisions in accordance with known thoracoscopic cardiac surgical technique. In some cases, the heart will be stopped and the patient will be placed on cardiopulmonary bypass. In other cases, the procedure may be performed on the beating heart, without cardiopulmonary bypass, in accordance with the currently known or hereafter devised techniques for such beating heart surgery.

Figure 7A:
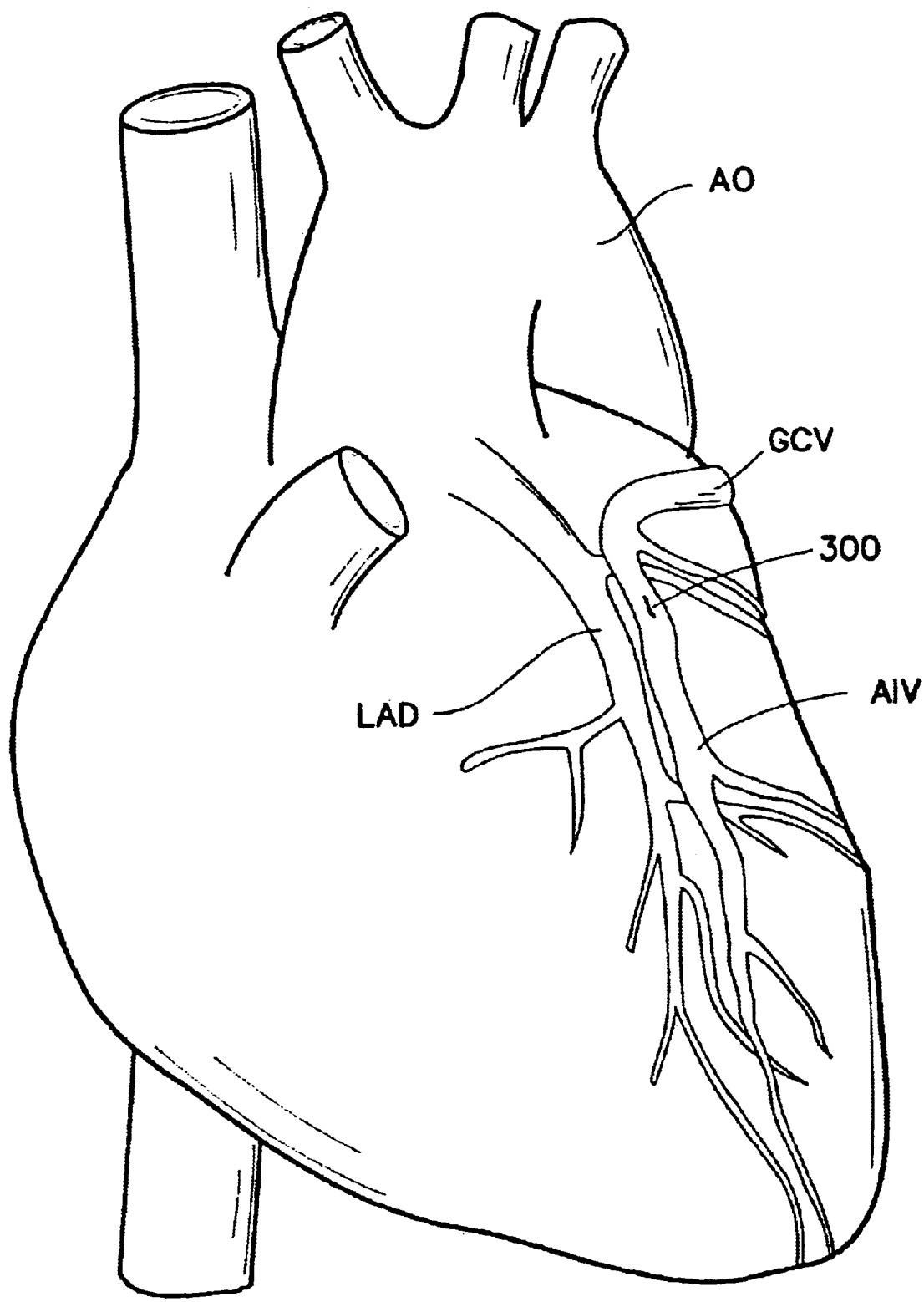
FIGS. 7a–7f show, in stepwise fashion, an intraoperative, surgical method for blocking blood flow through a vein into which arterial blood has been caused to flow in accordance with the present invention.
Figure 7B:
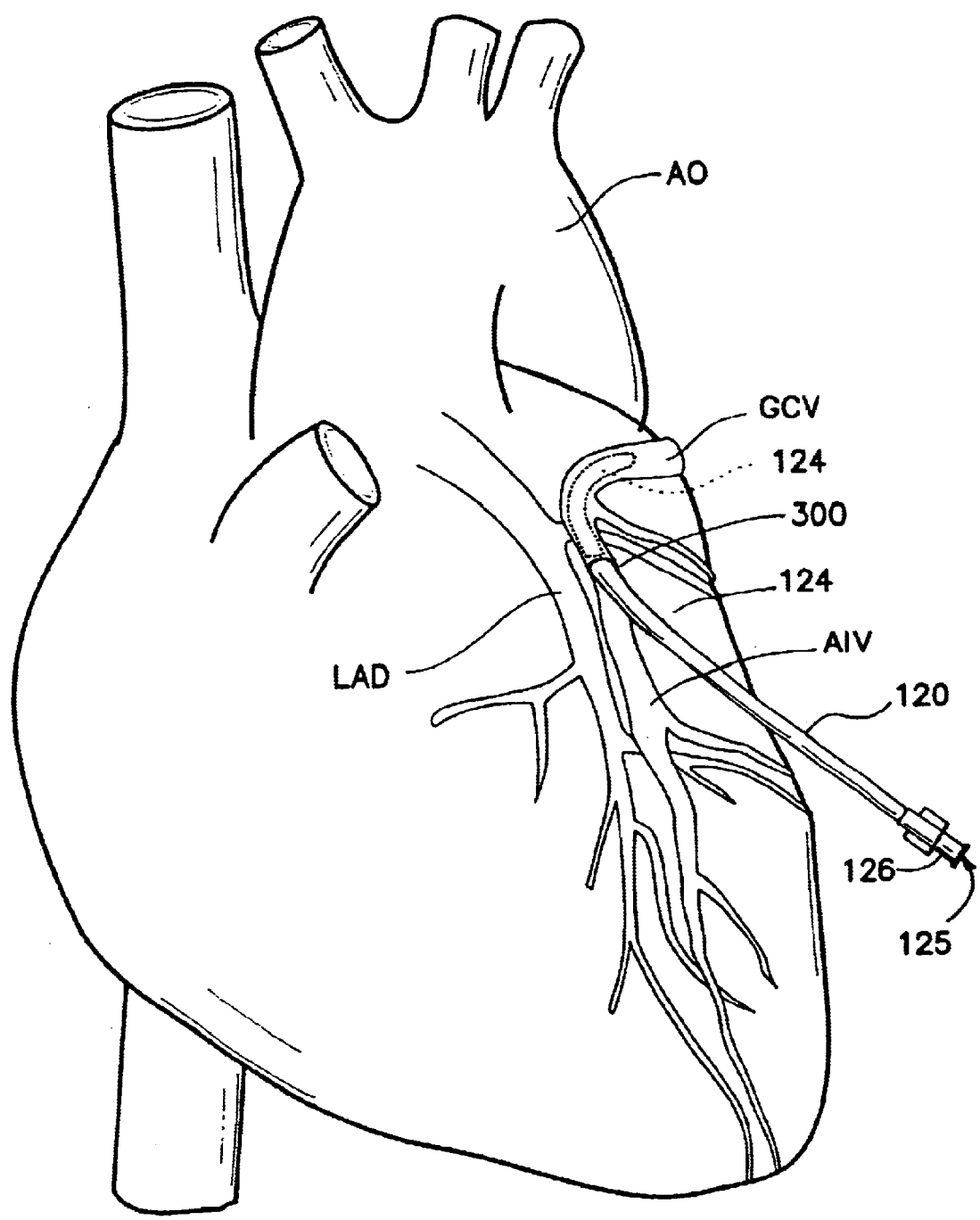

As shown in FIG. 7b, a small venotomy incision 300 is formed in the epicardial aspect of the anterior interventricular vein AIV. In cases were the patient's heart has been stopped and the patient has been placed on cardiopulmonary bypass, there will be little or no blood flow through the coronary veins and thus there will be no need for local hemostasis during or after creation of the venotomy incision 300. However, in cases where the procedure is performed on a beating heart, it will be desirable to compress or occlude the Anterior Interventricular Vein AIV at a location distal to the site of the venotomy incision 300 to prevent blood from being lost through the venotomy incision 300. Examples of commercially available devices that are usable for this purpose are referred to hereabove.

The blocker device 10 of the present invention is either pre-loaded in a venotomy delivery catheter 120 at the time of manufacturer or, alternatively, a blocker introduction device 200 of the present invention is attached to the proximal hub 126 of a venotomy delivery catheter 120 and the blocker device 10 is then loaded into the venotomy delivery catheter 120 using the technique described in detail hereabove.

Thereafter, as shown in FIG. 7b, the distal end of a venotomy delivery catheter 120 which has a blocker 10 contained within its lumen 125 is inserted through the venotomy opening 300 and into the Anterior Intraventricular Vein AIV and is advanced in the distal direction until the distal end of the delivery catheter body 124 is positioned within the Great Cardiac Vein GCV, proximal to the location of the venotomy incision 300.

Figure 7C:
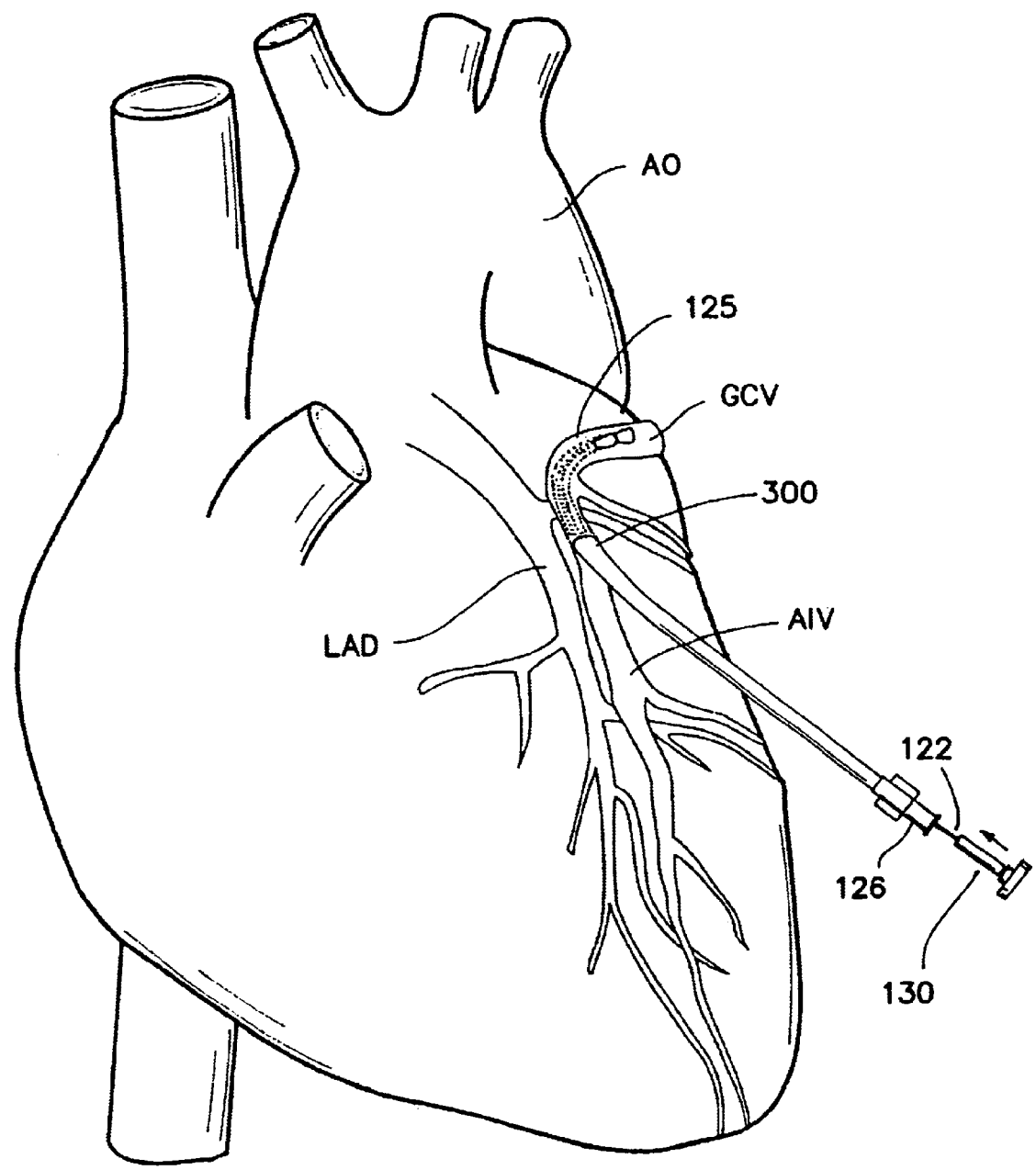

Thereafter, as shown in FIG. 7c, the pusher device 122 is inserted through the proximal Luer hub 126 of the venotomy delivery catheter 120 and is advanced through its lumen 125 until the handle 130 of the pusher 122 abuts against the hub 126 of the venotomy delivery catheter 120, thereby forcing the blocker 10 out of the distal end of the venotomy delivery catheter 120 and into the lumen of the Great Cardiac Vein GCV. It will be appreciated that, an alternative approach would be to advance the pusher to a position approximately one blocker length proximal to the distal end of the catheter body 124 (i.e., such that the distal tip of the blocker 10 is flush with the distal end of the catheter body 124). Thereafter, the pusher 122 is maintained in substantially fixed longitudinal position while and the catheter body 124 is retracted in the proximal direction until the handle 130 of the pusher 122 abuts against the hub 126 of the catheter, thereby causing the blocker 10 to be expelled out of the distal end of the catheter body 124 and into the great cardiac vein GCV.

Figure 7D:
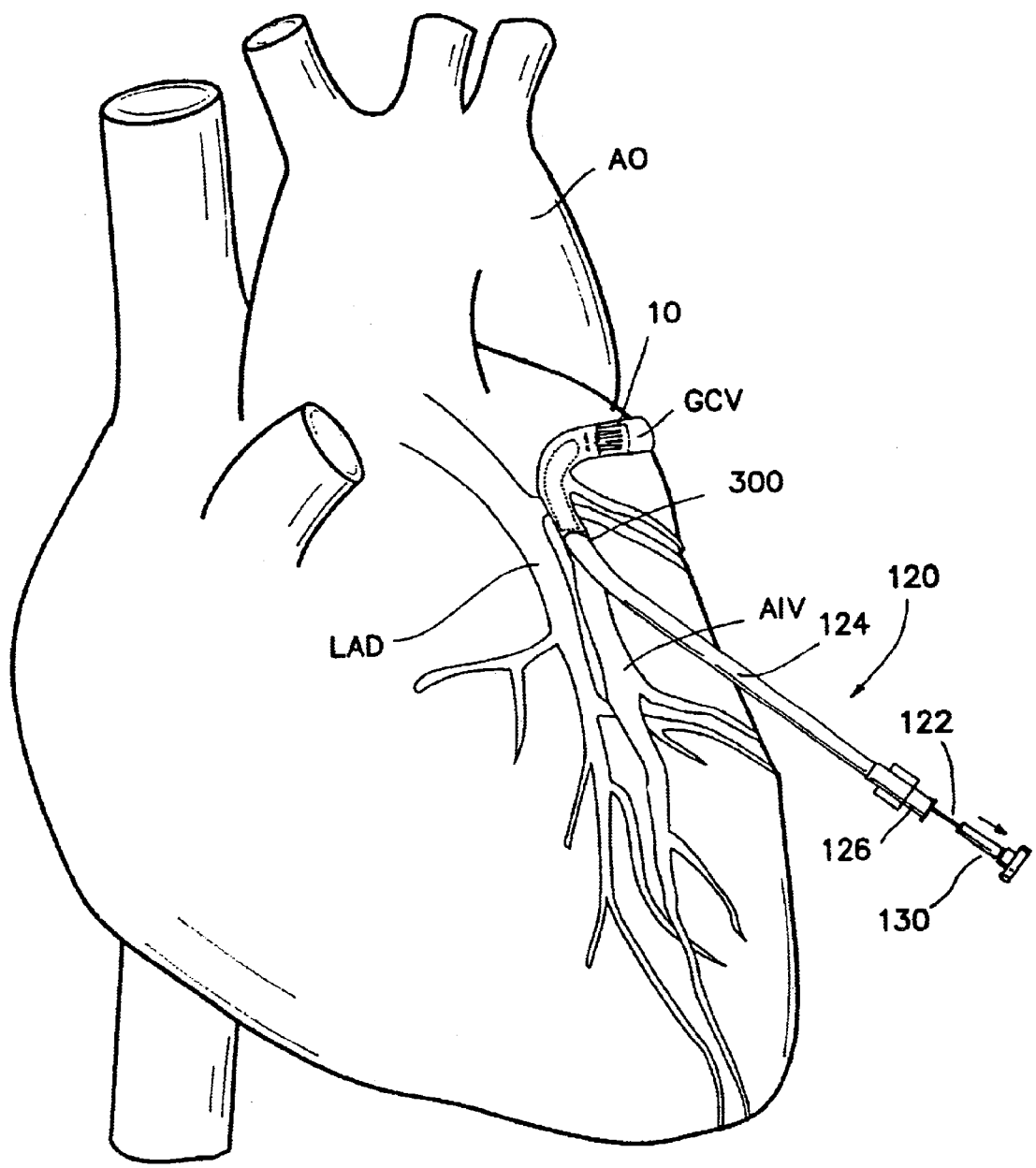

As shown in FIG. 7d, after the blocker 10 has been expelled out of the distal end of the delivery catheter body 124, the blocker 10 is no longer constrained by the surrounding catheter 100 and, thus, the blocker will radially self-expand within the lumen of the Great Cardiac Vein GCV. The blocker is sized such that, when the blocker 10 has fully expanded, its periphery will firmly coapt with the wall of the Great Cardiac Vein GCV and the end cap 16 of the blocker will be positioned transversely across the lumen of the great cardiac vein GCV so as to block blood from flowing through the Great Cardiac Vein GCV at that location. The venotomy delivery catheter 120 and pusher 122 (as well as any guidewire that may optionally have been used) are then extracted and removed, leaving the blocker 10 in place.

In this example, the blocker is shown as having been implanted with the outer surface OS of its end cap 14 directed counter to the proximally directed arterial blood flow. It will be appreciated, however, that the bocker 10 may in some applications be turned end-to-end 180 degrees such that the inner surface of the end cap 14 is directed counter to the direction of bloodflow.

Figure 7E:
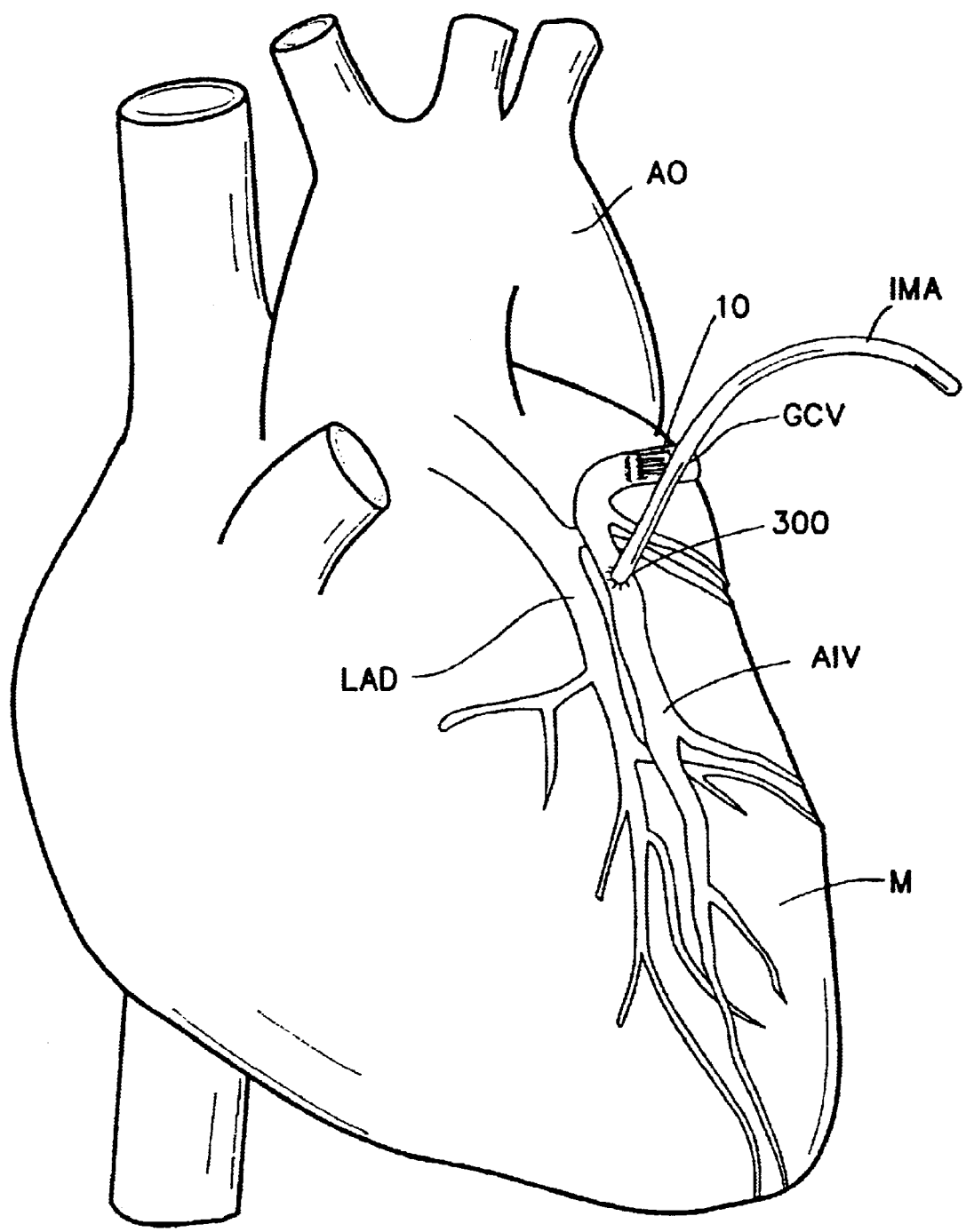
Figure 7F:
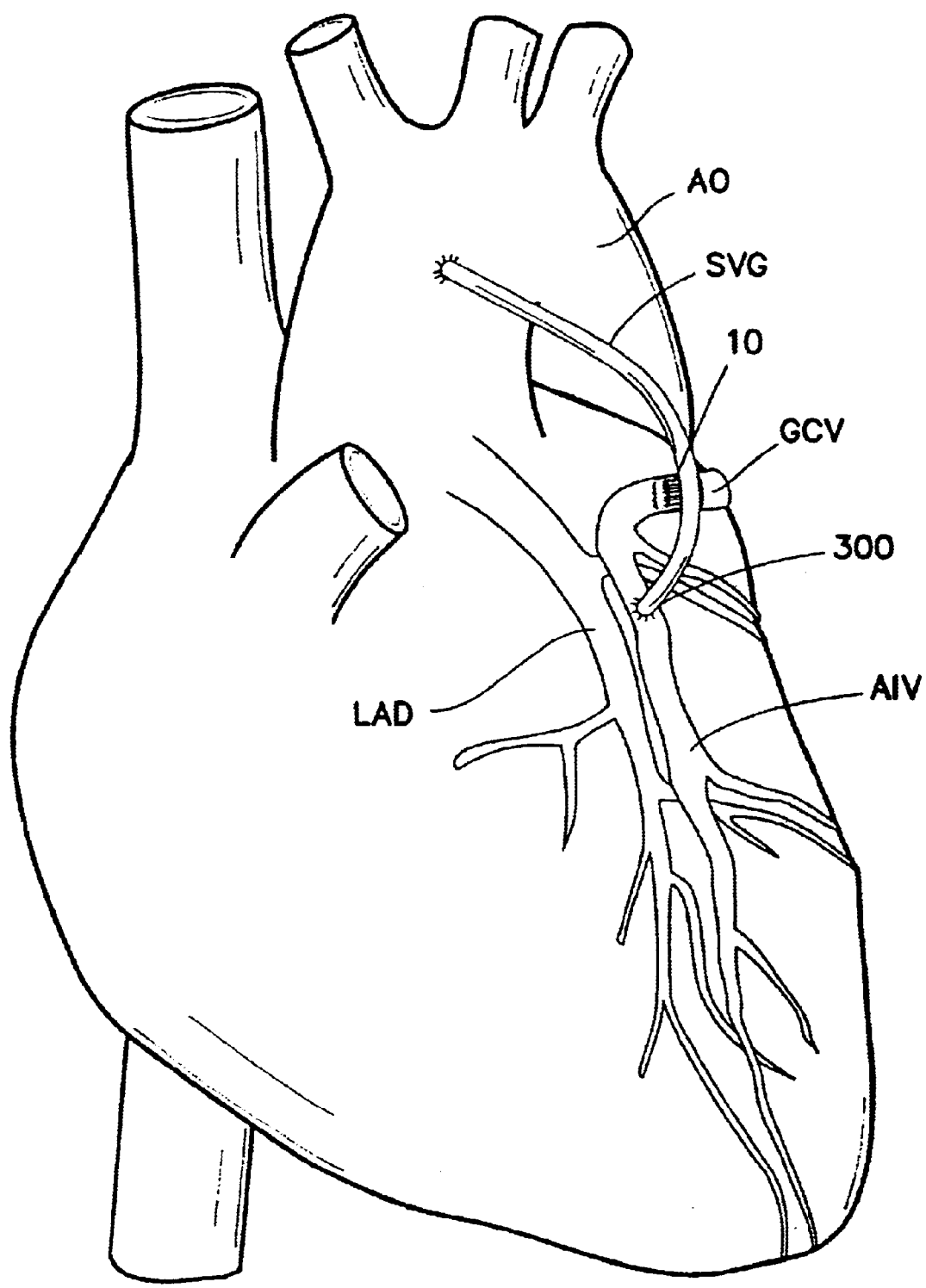

Thereafter, as shown alternatively in FIGS. 7e and 7f, a vascular grafting procedure is carried out to connect an arterial blood carrying graft to the venotomy incision 300. FIG. 7e illustrates a procedure wherein an internal mammary artery graft is utilized, while FIG. 7f illustrates a procedure wherein saphenous vein graft is used.

Specifically, with respect to the showing of FIG. 7e, the internal mammary artery is transected and dissected free from the patient's chest wall, and the free end of the internal memory artery IMA is translocated into apposition with the anterior interventricular vein AIV and is anastomosed, in end-to-side fashion, to the venotomy incision 300. In this manner, arterial blood is caused to flow from the internal memory artery IMA and into the anterior interventricular vein AIV. After the arterial blood enters the anterior interventricular vein AIV, it flows in the distal direction, opposite the direction of normal venous flow within that vein, due to the fact that the blocker 10 has been implanted within the great cardiac vein GCV. As a result, arterial blood is caused to perfuse the region of myocardium that was previously rendered ischemic due to an obstruction in the neighboring left anterior descending coronary artery LAD.

FIG. 7f shows an alternative vascular grafting procedure wherein a sapheonus vein graft SVG has been harvested from the patient's leg and. one end of the saphenous vein graft SVG has been anastomosed to an opening formed in the patient's aorta while the other end has been anastomosed to the venotomy incision 300 that had been previously formed in the patient's Anterior Interventricular Vein AIV. In this manner, arterial blood is caused to flow from the aorta, through the saphenous vein graft SVG and into the Anterior Interventricular Vein AIV. After the arterial blood has entered the Anterior Interventricular Vein AIV, it flows in the distal direction, opposite the direction of normal venous flow within that vein, due to the fact that the blocker 10 has been implanted within the great cardiac vein GCV. As a result, arterial blood is caused to perfuse the region of myocardium that was previously rendered ischemic due to an obstruction in the neighboring left anterior descending coronary artery LAD.

Although in this example a single venotomy incision 300 has been used for both introduction of the venotomy delivery catheter 120 and attachment of the arterial graft SVG or IMA, in some applications, a first venotomy incision may be used for introduction of the venotomy delivery catheter 120 and a second venotomy incision may be used for attachment of the arterial graft SVG or IMA. The first venotomy incision is then closed by suturing, patch graft or other suitable means after the delivery catheter 120 has been removed. In such cases where two separate venotomy incisions are used, the blocker need not be implanted before anastomosis of the arterial graft SVG or IMA to the vein and may, instead, be implanted after the anastomosis of the graft SVG or IMA to the vein has been completed.

It is to be understood and appreciated that the invention has been described herein with reference to certain presently preferred embodiments and examples only, and no effort has been made to exhaustively describe all possible embodiments and examples of the invention. Indeed, as those killed in the art will appreciate, various additions, deletions, modifications and variations may be made to the particular embodiments and examples described hereabove without departing from the intended spirit and scope of the invention. For example, where this patent application has listed the steps of a method or procedure in a specific order, it may be possible unless otherwise specified to change the order in which some steps are performed, and it is intended that the particular steps of the method or procedure claims set forth herebelow not be construed as being order-specific unless such order specificity is expressly stated in the claim.

Another example is that, although the preferred blocker device 10 described in this application is a self-expanding type, the frame 12 of the blocker device 10 may alternatively be made of plastically deformable material and the blocker device 10 may be thereby converted to a pressure-expandable or "balloon-expandable" apparatus. Another example is that, although the detailed descriptions set forth above referred to a radially expandable, implantable blocker device, it will be appreciated that the methods of the present invention may be carried out using any transluminally insertable apparatus for fusing, closing, blocking, constricting or otherwise preventing or restricting flow through the vein lumen, including but not limited to other types of implantable blockers, occluders, intraluminal suturing devices, embolization members and/or the devices described in U.S. Pat. No. 6,071,292 (Makower et al.) entitled Transluminal Methods and Devices for Closing, Forming Attachments to, and/or Forming Anastomotic Junctions in Luminal Anatomical Structures and PCT International Publication Nos. WO97/27893 (Evard, et al.) entitled Methods and Apparatus for Blocking Flow Through Blood Vessels and WO99/49793 (Flaherty et al.) entitled Catheters, Systems and Methods for Percutaneous In Situ Arterio-Venous Bypass, the entire disclosures of which are expressly incorporated herein by reference.

Accordingly, it is intended that all such additions, deletions, modifications and variations be included within the scope of the following claims.

We claim:

1. A system for facilitating flow of blood through the lumen of a blood vessel, said system comprising:
    a tubular graft that is attachable to the blood vessel at a first location; and
    a lumen occluding device that is implantable in the lumen of the blood vessel so as to facilitate a flow of blood from the graft, into the blood vessel, and through the blood vessel in a desired direction, said lumen occluding device comprising;
        a generally cylindrical frame that is disposable in a radially compact configuration of a first diameter and is transitionable to a radially expanded configuration of a second diameter; and
        a lumen occluding barrier attached to the frame, said lumen occluding barrier being configured such that, when the device is implanted in the lumen of a blood vessel with the frame in its radially expanded configuration, the occluding barrier will substantially block blood flow through that blood vessel lumen.

2. A system according to claim 1 further comprising:
    a delivery catheter that comprises an elongate tubular catheter body having a lumen extending longitudinally therethrough;
    the lumen occluding device being a) positionable within the lumen of the delivery catheter when the lumen occluding device is in its radially collapsed configuration and b) expellable out of the catheter and into the lumen of a blood vessel in which the catheter is positioned, such that the lumen occluding device will assume its radially expanded configuration and become implanted within the lumen of the blood vessel.

3. A system according to claim 2 wherein the delivery catheter has a length of 40–125 cm.

4. A system according to claim 2 wherein the delivery catheter has a length of 5–20 cm.

5. A system according to claim 2 wherein the delivery catheter further comprises:
    a location identifier which provides an indication of the catheter within the blood vessel.

6. A system according to claim 5 wherein the location identifier comprises a marker that can be imaged by a separate imaging apparatus.

7. A system according to claim 6 wherein the marker is radiopaque so as to be radiographically imageable.

8. A system according to claim 6 wherein the marker is reflective of ultrasound so as to be imageable by ultrasound.

9. A system according to claim 5 wherein the location identifier is an energy emitting element.

10. A system according to claim 9 wherein the energy emitting element emits ultrasound.

11. A system according to claim 2 further comprising a pusher that is advanceable through the lumen of the delivery catheter to push the lumen occluding device out of the delivery catheter.

12. A system according to claim 11 wherein the pusher comprises an elongate member having a lumen extending longitudinally therethrough such that the pusher may be advanced over a guidewire.

13. A system according to claim 11 wherein the pusher comprises an elongate member having a proximal end to which a proximal hub member is attached, and wherein the length of the elongate member is sized relative to the length of the delivery catheter such that when the pusher is advanced distally through the catheter lumen the distal end of the pusher will not protrude beyond the distal end of the catheter body.

14. A system according to claim 2 wherein the lumen occluding device was placed in its radially compact configuration within the lumen of the delivery catheter prior to insertion of the delivery catheter into the blood vessel.

15. A system according to claim 2 wherein the lumen occluding device was placed in its radially compact configuration within the lumen of the delivery catheter after insertion of the delivery catheter into the blood vessel.

16. A system according to claim 2 further comprising:
    a lumen occluding device introduction apparatus that is useable to facilitate radial collapsing of the lumen occluding device and introduction of the radially collapsed lumen occluding device into the lumen of the delivery catheter.

17. A system according to claim 16 wherein the lumen occluding device introduction apparatus comprises:
    a rigid body having a lumen extending longitudinally therethrough, the distal end of the rigid body being connectable to the proximal end of the delivery catheter and the lumen of the blocker introduction apparatus being tapered from a first diameter at its proximal end to a second diameter at its distal end, said first diameter being larger than the diameter of the catheter lumen and said second diameter being approximately the same as the diameter of the catheter lumen.

18. A system according to claim 11 wherein the delivery catheter is less than 20 cm in length and insertable into a substantially straight segment of vein and wherein the pusher, when inserted into the lumen of the delivery catheter, not protrude out of the distal end of the delivery catheter.

19. A system according to claim 11 wherein the deliver catheter is greater than 20 cm in length and insertable into substantially tortuous vasculature wherein the pusher is longer than the catheter in length such that even when the catheter is positioned in tortuous vasculature the pusher may be advanced through the catheter lumen to a position where the distal end of the pusher is substantially coterminus with the distal end of the catheter.

20. A system according to claim 11 wherein the distal end of the pusher is imageable to facilitate monitoring of the position of the distal end of the pusher relative to the distal end of the catheter.

21. A system according to claim 1 wherein a guidewire passage aperture is formed in said occluding barrier so that a guidewire may pass therethrough, the device being thereby advanceable over a guidewire that has previously been inserted into the blood vessel.

22. A system for blocking blood flow through the lumen of a blood vessel, said system comprising:
   a) a delivery catheter that comprises an elongate tubular catheter body having a lumen extending longitudinally therethrough;
   b) a lumen occluding device that is positionable within the lumen of the catheter while in a radially collapsed configuration and thereafter expellable out of the catheter and into the lumen of a blood vessel in which the catheter is positioned, such that the lumen occluding device will assume its radially expanded configuration and become implanted within the lumen of the blood vessel, said lumen occluding device comprising
      i) a generally cylindrical frame that is disposable in a radially compact configuration of a first diameter and is transitionable to a radially expanded configuration of a second diameter; and
      ii) a lumen occluding barrier attached to the frame, said lumen occluding barrier being configured such that, when the device is implanted in the lumen of a blood vessel with the frame in its radially expanded configuration, the occluding barrier will substantially block blood flow through that blood vessel lumen, a guidewire passage aperture being formed in said occluding barrier so that a guidewire may pass therethrough, the device being thereby advanceable over a guidewire that has previously been inserted into the blood vessel; and
   a lumen occluding device introduction apparatus comprising a substantially rigid body having a tapered lumen, said tapered lumen having a first end and a second end, the first end of said tapered lumen being larger in diameter than the second end, said introduction device being connectable to the delivery catheter;
   said lumen occluding device being insertable, while in its radially expanded configuration, into the first end of the tapered lumen of the introduction apparatus and, thereafter, advanceable from the first end of the tapered lumen to the second end of the tapered lumen such that the decrease in diameter of the tapered lumen will compress the lumen occluding device to its radially collapsed configuration, said lumen occluding device being thereafter advanceable, while in its radially collapsed configuration, into the lumen of the delivery catheter.

23. A system according to claim 22 wherein the delivery catheter has a length of 40–125 cm.

24. A system according to claim 22 wherein the delivery catheter has a length of 5–20 cm.

25. A system according to claim 22 wherein the delivery catheter further comprises:
   a location identifier which provides an indication of the catheter within the blood vessel.

26. A system according to claim 25 wherein the location identifier comprises a marker that can be imaged by a separate imaging apparatus.

27. A system according to claim 26 wherein the marker is radiopaque so as to be radiographically imageable.

28. A system according to claim 26 wherein the marker is reflective of ultrasound so as to be imageable by ultrasound.

29. A system according to claim 25 wherein the location identifier is an energy emitting element.

30. A system according to claim 29 wherein the energy emitting element emits ultrasound.

31. A system according to claim 22 further comprising a pusher that is advanceable through the lumen of the delivery catheter to push the lumen occluding device out of the delivery catheter.

32. A system according to claim 31 wherein the pusher comprises an elongate member having a lumen extending longitudinally therethrough such that the pusher may be advanced over a guidewire.

33. A system according to claim 31 wherein the pusher comprises an elongate member having a proximal end to which a proximal hub member is attached, and wherein the length of the elongate member is sized relative to the length of the delivery catheter such that when the pusher is advanced distally through the catheter lumen until the proximal hub of the pusher abuts against the delivery catheter, the distal end of the pusher will not protrude beyond the distal end of the catheter body.

34. A system according to claim 22 wherein the lumen occluding device is placed in its radially compact configuration within the lumen of the delivery catheter prior to insertion of the delivery catheter into the blood vessel.

35. A system according to claim 32 wherein the lumen occluding device is placed in its radially compact configuration within the lumen of the delivery catheter after insertion of the delivery catheter into the blood vessel.

36. A system according to claim 22 wherein the lumen occluding device introduction apparatus comprises:
   a rigid body having a lumen extending longitudinally therethrough, the distal end of the rigid body being connectable to the proximal end of the delivery catheter and the lumen of the blocker introduction apparatus being tapered from a first diameter at its proximal end to a second diameter at its distal end, said first diameter being larger than the diameter of the catheter lumen and said second diameter being approximately the same as the diameter of the catheter lumen.

37. A system according to claim 31 wherein the delivery catheter is less than 20 cm in length and is insertable into a substantially straight segment of vein and wherein the pusher, when fully inserted into the lumen of the delivery catheter, does not protrude out of the distal end of the delivery catheter.

* * * * *